(12) United States Patent
Oda et al.

(10) Patent No.: US 6,197,990 B1
(45) Date of Patent: Mar. 6, 2001

(54) PROCESS FOR THE PREPARATION OF CYCLOPENTADIENYL METAL SALT AND PROCESS FOR THE PREPARATION OF DERIVATIVE OF CYCLOPENTADIENE USING THE SAME

(75) Inventors: Yoshiaki Oda, Toyonaka; Kazuhiro Yamauchi, Ibaraki; Hidenori Hanaoka, Osaka; Hiroshi Souda, Ibaraki, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/341,498

(22) PCT Filed: Jan. 14, 1998

(86) PCT No.: PCT/TP98/00110

§ 371 Date: Jul. 13, 1999

§ 102(e) Date: Jul. 13, 1999

(87) PCT Pub. No.: WO98/30567

PCT Pub. Date: Jul. 16, 1998

(30) Foreign Application Priority Data

Jan. 14, 1997 (JP) ........................................ 9-005036
Jan. 14, 1997 (JP) ........................................ 9-005037

(51) Int. Cl.[7] ........................................................ C07F 7/04
(52) U.S. Cl. ........................ 556/478; 556/87; 585/350; 585/390
(58) Field of Search .................................. 585/350, 390; 556/87, 478

(56) References Cited

U.S. PATENT DOCUMENTS 6,046,346 * 4/2000 Yokoyama et al. .................. 556/53
6,066,704 * 5/2000 Katayama et al. .................. 526/127

FOREIGN PATENT DOCUMENTS 6-279477   10/1994   (JP) .

OTHER PUBLICATIONS

Wiesenfeldt et al., Journal of Organometallic Chemistry, vol. 369, pp. 359–370, 1989.*

Chem. Ber., 124, 1991, pp. 2185–2190, "Mono–, Bis—and Tris (cyclopentadienyl) Compounds—Syntheses of New Polydentate Ligands and their Molybdenum and Tungsten Complexes", Plenio, H.

Journal of Organometallic Chemistry, 495, 1995, pp. 195–202, "Synthesis and Characterization of Titanium Complexes Containing the 1–(3–Butenyl)–2,3,4,5–Tetramethylcyclopentadienyl Ligand", Okuda, J. et al.

* cited by examiner

Primary Examiner—Porfirio Nazario-Gonzalez
(74) Attorney, Agent, or Firm—Sughrue, Mion, Zinn, Macpeak & Seas, PLLC

(57) ABSTRACT

A cyclopentadienyl metal salt is prepared by reacting a cyclopentadiene and a metal hydride in the presence of an amine compound. Furthermore, a derivative of a cyclopentadiene in which a phenyl group is bonded to its cyclopentadienyl moiety through an element of the 14 group of the Periodic Table is prepared using such a reaction.

20 Claims, No Drawings

PROCESS FOR THE PREPARATION OF CYCLOPENTADIENYL METAL SALT AND PROCESS FOR THE PREPARATION OF DERIVATIVE OF CYCLOPENTADIENE USING THE SAME

FIELD OF THE INVENTION

The present invention relates to a process for the preparation of a cyclopentadienyl metal salt and a process for the preparation of a cyclopentadiene derivative using the same.

BACKGROUND ART

Cyclopentadienyl metal salts and derivatives of cyclopentadiene derived from such metal salts are important intermediates which are used in various fields such as the preparation of medicines, agrochemicals, metallocenes, etc. An effective process for the preparation of cyclopentadienyl metal salts comprises removing hydrogen atoms from cyclopentadiene with bases to synthesize corresponding metal salts, and for example, such a process using butyl lithium is known (J. Organomet. Chem., 462, 1993, 57–67).

However, the process using butyl lithium has disadvantages such that (1) used reagents are expensive, (2) it requires low-temperature facilities to perform the reaction, and (3) the reaction should be carried out at the low concentration of reagents in an industrial scale, and thus the productivity decreases, since the desired product cannot effectively be obtained if the reaction is not carried out at a low temperature, although the amount of reaction heat is large. As a matter of course, cyclopentadiene derivatives derived from cyclopentadienyl metal salts have the same problems.

Also, a process using an alkali metal hydride is known. However, this process has disadvantages such that (1) the kinds of substrates are extremely limited, (2) mineral oils, which are usually contained as a stabilizer in marketed alkali metal hydrides, should be beforehand removed, and thus the use of the alkali metal hydrides is unfavorable from the viewpoint of disaster measures, and the number of process steps in the industrial production.

DISCLOSURE OF THE INVENTION

In view of the above circumstances, the present inventors extensively studied a process which can easily produce a cyclopentadienyl metal salt without the use of expensive reagents and low-temperature facilities, and has no substrate specificity. As a result, it has been found that such an object can be accomplished by the reaction of a cyclopentadiene and a metal hydride in the presence of an amine compound, and thus the present invention has been completed.

Accordingly, the present invention provides 1. a process for the preparation of a cyclopentadienyl metal salt comprising the step of reacting a cyclopentadiene and a metal hydride in the presence of an amine compound, and
2. a process for the preparation of a cyclopentadiene derivative of the formula (3):

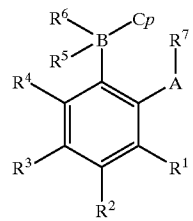

(3)

wherein
A is an atom of the 16 group of the Periodic Table,
B is an atom of the 14 group of the Periodic Table,
$R^1$, $R^2$, $R^3$, $R^4$, $R^5$ and $R^6$ are the same or different and independently represent a hydrogen atom, a fluorine atom, a $C_1$–$C_{20}$ alkyl group which may optionally be substituted with a fluorine atom, a $C_7$–$C_{20}$ aralkyl group which may optionally be substituted with a fluorine atom, a $C_6$–$C_{20}$ aryl group which may optionally be substituted with a fluorine atom, a $C_1$–$C_{20}$ substituted silyl group, a $C_1$–$C_{20}$ alkoxyl group which may optionally be substituted with a fluorine atom, a $C_7$–$C_{20}$ aralkyloxyl group which may optionally be substituted with a fluorine atom, a $C_6$–$C_{20}$ aryloxyl group which may optionally be substituted with a fluorine atom, or a $C_2$–$C_{20}$ di-substituted amino group which may optionally be substituted with a fluorine atom, provided that any two or more of $R^1$, $R^2$, $R^3$, $R^4$, $R^5$ and $R^6$ may together form a ring,
$R^7$ is a hydrocarbon group which may optionally be substituted with a fluorine atom, or a tri-substituted silyl group, and
Cp is a cyclopetadiene ring comprising the step of reacting a halide compound of the formula (1):

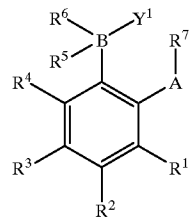

(1)

wherein A, B, $R^1$, $R^2$, $R^3$, $R^4$, $R^5$, $R^6$ and R7 are the same as defined above, and $Y^1$ is a chlorine atom, a bromine atom or an iodine atom
with a cyclopentadiene of the formula (2):

HCp (2)

wherein Cp is the same as defined above, in the presence of a metal hydride and an amine compound.

Here, the process according to the first aspect of the present invention, that is, the preparation process of a cyclopentadienyl metal salt by the reaction of a cyclopentadiene and a metal hydride in the presence of an amine compound, will be explained.

Cyclopentadienes used in the present invention may be any compounds having a cyclopentadienyl moiety. For example, a cyclopentadiene of the formula (2), which is used in the processes according to the first and second aspects of the present invention, may be a compound of the formula (2a):

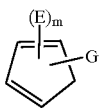

wherein m is an integer of 0 to 5, E groups are the same or different and independently represent a $C_1$–$C_8$ alkyl group, a phenyl group, a naphthyl group, or a tri-substituted silyl group having substituents selected from the group consisting of a $C_1$–$C_4$ alkyl group and a phenyl group, provided that, when two E groups are present on adjacent carbon atoms, they may be bonded at their ends to form a benzene ring, a cyclohexane ring or a cyclohexene ring, which is condensed with the cyclopentadienyl ring, G is a hydrogen atom when m is 5, or when m is 0 to 4, G is a hydrogen atom or a group of the formula (2b):

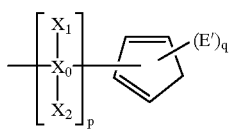

wherein p is an integer of 1 or 2, q is an integer of 0 to 4, $X_0$ is a carbon atom or a silicon atom, $X_1$ and $X_2$ are the same or different and independently represent a hydrogen atom, a $C_1$–$C_4$ alkyl group or a phenyl group, E' is a substituent selected from those defined for E, provided that when $X_0$ is a silicon atom, $X_1$ and $X_2$ are not hydrogen atoms.

Herein, the cyclopentadienyl group includes a mixture of its tautomers, which is usually obtained. The chemical structures in this specification represent a part of tautomers as typical examples.

Examples of cyclopentadienes, which are compounds having a cyclopentadienyl moiety, include cyclopentadiene compounds such as cyclopentadiene, methylcyclopentadiene, dimethylcyclopentadiene, trimethylcyclopentadiene, tetramethylcyclopentadiene, pentamethylcyclopentadiene, ethylcyclopentadiene, n-propylcyclopentadiene, isopropylcyclopentadiene, n-butylcyclopentadiene, sec.-butylcyclopentadiene, tert.-butylcyclopentadiene, n-pentylcyclopentadiene, neopentylcyclopentadiene, n-hexylcyclopentadiene, n-octylcyclopentadiene, phenylcyclopentadiene, naphthylcyclopentadiene, trimethylsilylcyclopentadiene, triethylsilylcyclopentadiene, tert.-butyldimethylsilylcyclopentadiene, etc.;

indene compounds such as indene, methylindene, dimethylindene, ethylindene, n-propylindene, isopropyl indene, n-butylindene, sec.-butylindene, tert.-butylindene, n-pentylindene, neopentylindene, n-hexylindene, n-octylindene, n-decylindene, phenylindene, methylphenylindene, naphthylindene, trimethylsilylindene, triethylsilylindene, tert.-butyldimethylsilylindene, tetrahydroindene, etc.;

fluorene compounds such as fluorene, methylfluorene, ethylfluorene, n-propylfluorene, isopropylfluorene, n-butylfluorene, sec.-butylfluorene, tert.-butylfluorene, n-pentylfluorene, neopentylfluorene, n-hexylfluorene, n-octylfluorene, n-decylfluorene, n-dodecylfluorene, phenylfluorene, naphthylfluorene, trimethylsilylfluorene, triethylsilylfluorene, tert.-butyldimethylsilylfluorene, etc.;

biscyclopentadiene compounds such as biscyclopentadienylmethane, biscyclopentadienylethane, biscyclopentadienylpropane, biscyclopentadienylbutane, biscyclopentadienylpentane, biscyclopentadienylhexane, biscyclopentadienyldimethylsilane, biscyclopentadienyldiphenylsilane, bismethylcyclopentadienyldimethylsilane, bisdimethylcyclopentadienyldimethylsilane, bistrimethylcyclopentadienyldimethylsilane, bistetramethylcyclopentadienyldimethylsilane, biscyclopentadienyltetramethyldisilane, etc.;

bisindene compounds such as bisindenylmethane, bisindenylethane, bisindenylpropane, bisindenylbutane, bisindenylpentane, bisindenylhexane, bisindenyldimethylsilane, bisindenyldiphenylsilane, bismethylindenyldimethylsilane, bisdimethylindenyldimethylsilane, bisindenyltetramethyldisilane, etc.;

bisfluorene compounds such as bisfluorenylmathane, bisfluorenylethane, bisfluorenylpropane, bisfluorenylbutane, bisfluorenylpentane, bisfluorenylhexane, bisfluorenyldimethylsilane, bisfluorenyldiphenylsilane, bisfluorenyltetramethyldisilane, etc.;

complex compounds such as cyclopentadienylindenylmethane, cyclopentadienylindenylethane, cyclopentadienylindenylpropane, cyclopentadienylindenylbutane, cyclopentadienylindenylpentane, cyclopentadienylindenylhexane, cyclopentadienylindenyldimethylsilane, cyclopentadienylindenyldiphenylsilane, methylcyclopentadienylindenyldimethylsilane, dimethylcyclopentadienylindenyldimethylsilane, trimethylcyclopentadienylindenyldimethylsilane, tetramethylcyclopentadienylindenyldimethylsilane, cyclopentadienylindenyltetramethyldisilane, cyclopentadienylfluorenylmethane, cyclopentadienylfluorenylethane, cyclopentadienylfluorenylpropane, cyclopentadienylfluorenylbutane, cyclopentadienylfluorenylpentane, cyclopentadienylfluorenylhexane, cyclopentadienylfluorenyldimethylsilane, cyclopentadienylfluorenyldiphenylsilane, methylcyclopentadienylfluorenyldimethylsilane, dimethylcyclopentadienylfluorenyldimethylsilane, trimethylcyclopentadienylfluorenyldimethylsilane, tetramethylcyclopentadienylfluorenyldimethylsilane, cyclopentadienylfluorenyltetramethyldisilane, etc.

The process of the present invention can easily produce desired compounds at a high yield, when cyclopentadiene compounds having two or more substituents are used.

Examples of metal hydrides include alkali metal hydrides such as lithium hydride, sodium hydride, potassium hydride, etc.; and alkaline earth metal hydrides such as calcium hydride, etc. The amount of a metal hydride is usually from 0.5 to 3 moles, preferably from 0.9 to 2.0 moles, per one mole of the compound (2). Sodium hydride and potassium hydride can be used in the form of a marketed product containing mineral oils, although they may be used after washing the mineral oils off with hydrocarbon solvents such as hexane, etc.

As an amine compound, a compound of the following formula (4) is exemplified:

$$Q_1Q_2Q_3N$$

wherein $Q_1$, $Q_2$ and $Q_3$ are the same or different and independently represent a hydrogen atom, a $C_1$–$C_8$ alkyl group, or a $C_3$–$C_8$ cycloalkyl group; or a phenyl group, a naphthyl group, a benzyl group, a naphthylmethyl group or a pyridyl group, which may optionally be substituted with at least one substituent selected from the group consisting of a halogen atom, a $C_1$–$C_4$ alkyl group, a $C_1$–$C_4$ alkoxyl group, a carboxyl group, a $C_1$–$C_4$ alkoxycarbonyl group, a nitro group, an amino group, a phenyl group, a naphthyl group and a benzyl group; or the terminals of $Q_1$ and $Q_2$ are bonded each other to form a $C_4$–$C_5$ alkylene group which may optionally be substituted with at least one $C_1$–$C_3$ alkyl group, or a group of the formula: (—$CH_2CH_2$)$_2$—O or (—$CH_2CH_2$)$_2$N—$Q_4$ in which $Q_4$ is a substituent selected from those defined for $Q_3$, or $Q_3$ may be an ethylene group or a group of the formula: —$(CH_2)_3$N= and bonded to a ring formed by $Q_2$ and $Q_3$, provided that $Q_1$, $Q_2$ and $Q_3$ are not hydrogen atoms at the same time.

Specific examples of amine compounds are primary amines including primary amines, for example, primary amines such as aniline, chloroaniline, bromoaniline, fluoroaniline, dichloroaniline, dibromoaniline, difluoroaniline, trichloroaniline, tribromoaniline, trifluoroaniline, tetrachloroaniline, tetrabromoaniline, tetrafluoroaniline, pentachloroaniline, pentafluoroaniline, nitroaniline, dinitroaniline, hydroxyaniline, phenylenediamine, anisidine, dimethoxyaniline., trimethoxyaniline, ethoxyaniline, diethoxyaniline, triethoxyaniline, n-propoxyaniline, isopropoxyaniline, n-butoxyaniline, sec.-butoxyaniline, isobutoxyaniline, tert.-butoxyaniline, phenoxyaniline, methylaniline, ethylaniline, n-propylaniline, isopropylaniline, n-butylaniline, sec.-butylaniline, isobutylaniline, tert.-butylaniline, dimethylaniline, diethylaniline, di-n-propylaniline, diisopropylaniline, di-n-butylaniline, di-sec.-butylaniline, diisobutylaniline, di-tert.-butylaniline, trimethylaniline, triethylaniline, diisopropylaniline, phenylaniline, benzylaniline, aminobenzoic acid, methyl aminobenzoate, ethyl aminobenzoate, n-propyl aminobenzoate, isopropyl aminobenzoate, n-butyl aminobenzoate, isobutyl aminobenzoate, sec.-butyl aminobenzoate, tert.-butyl aminobenzoate, etc.; as well as naphthylamine, naphthylmethylamine, benzylamine, propylamine, butylamine, pentylamine, hexylamine, cyclohexylamine, heptylamine, octylamine, 2-aminopyridine, 3-aminopyridine, 4-aminopyridine, etc., secondary amines such as N-methylaniline, N-ethylaniline, diphenylamine, N-methylchloroaniline, N-methylbromoaniline, N-methylfluoroaniline, N-methylanisidine, N-methylmethylaniline, N-methylethylaniline, N-methyl-n-propylaniline, N-methylisopropylaniline, diethylamine, diproylamine, diisopropylamine, dipentylamine, dihexylamine, dicyclohexylamine, diheptylamine, dioctylamine, morpholine, piperidine, 2,2,6,6-tetramethylpiperidine, pyrrolidine, 2-methylaminopyridine, 3-methylaminopyridine, 4-methylaminopyridine, etc., tertiary amines such as N,N-dimethylaniline, N,N-dimethylchloroaniline, N,N-dimethylbromoaniline, N,N-dimethylfluoroaniline, N,N-dimethylanisidine, N-methylmethylaniline, N,N-dimethylethylaniline, N,N-dimethyl-n-propylaniline, N,N-dimethylisopropylaniline, 2-dimethylaminopyridine, 3-dimethylaminopyridine, 4-dimethylaminopyridine, 1,4-diazabicyclo[2.2.2]octane, 1,5-diazabicyclo[4.3.0]non-5-ene, 1,8-diazabicyclo[5.4.0]undec-7-ene, etc.

Among them, primary and secondary amines are preferably used. More preferably, primary anilines are used.

The amount of an amine compound is usually from 0.001 to 2 moles, preferably from 0.01 to 0.5 mole, per one mole of a metal hydride.

The reaction is usually carried out in a solvent which is inactive to the reaction. Examples of solvents are aprotic solvents, for example, aromatic hydrocarbon solvents such as benzene, toluene, xylene, etc.; aliphatic hydrocarbon solvents such as pentane, hexane, heptane, octane cyclohexane, etc.; ether solvents such as diethyl ether, methyl tert.-butyl ether, tetrahydrofuran, 1,4-dioxane, etc.; amide solvents such as hexamethylphosphoric amide, dimethylformamide, dimethylacetamide, N-methylpyrrolidone, etc.; halogen-containing solvents such as chlorobenzene, dichlorobenzene, etc. These solvents may be used singly or in admixture of two or more solvents. The amount of a solvent is usually from 1 to 200 wt. parts, preferably from 3 to 30 wt. parts, per 1 wt. part of a cyclopentadiene.

To carry out the reaction, a cyclopentadiene, a metal hydride and an amine compound are mixed at the same time in a solvent, or a metal hydride and an amine compound are firstly mixed, and then a cyclopentadiene is added to the mixture.

A reaction temperature is not limited, but is preferably in a range in which no low-temperature facilities are necessary, for the industrial production. For example, a reaction temperature is usually in the range between 0 and 70° C., preferably between 10 and 60° C.

The above reaction effectively provides a desired cyclopentadienyl metal salt. The obtained cyclopentadienyl metal salt may be used in the form of a reaction mixture, or may be isolated from the reaction mixture. In general, the reaction mixture as such can satisfactorily be used.

Now, the process according to the second aspect of the present invention, that is, the preparation process of a cyclopentadiene derivative of the formula (3) by the reaction of a halide compound of the formula (1) and a cyclopentadiene of the formula (2) in the presence of a metal haride and an amine compound will be explained.

Examples of an atom of the 16 group of the Periodic Table, which is represented by "A" in the formula (1), include an oxygen atom, a sulfur atom, a selenium atom, etc. An oxygen atom and a sulfur atom are preferable, and an oxygen atom is more preferable.

Examples of an atom of the 14 group of the Periodic Table, which is represented by "B", include a carbon atom, a silicon atom, a germanium atom, etc. A carbon atom and a silicon atom are preferable.

Examples of a $C_1$–$C_{20}$ alkyl group for $R^1$, $R^2$, $R^3$, $R^4$, $R^5$ or $R^6$ include a methyl group, an ethyl group, a n-propyl group, an isopropyl group, a n-butyl group, a sec.-butyl group, a tert.-butyl group, a n-pentyl group, a neopentyl group, an amyl group, a n-hexyl group, a n-octyl group, a n-decyl group, a n-dodecyl group, a n-pentadecyl group, a n-eicosyl group, etc. Among them, a methyl group, an ethyl group, an isopropyl group, a tert.-butyl group and an amyl group are preferable.

Any one of these alkyl groups may optionally be substituted with one or more fluorine atoms. Examples of a fluorinated $C_1$–$C_{20}$ alkyl group include a fluoromethyl group, a difluoromethyl group, a trifluoromethyl group, a fluoroethyl group, a difluoroethyl group, a trifluoroethyl group, a tetrafluoroethyl group, a pentafluoroethyl group, a perfluoropropyl group, a perfluorobutyl group, a perfluoropentyl group, a perfluorohexyl group, a perfluorooctyl group, a perfluorodocecyl group, a perfluoropentadecyl group, a perfluoroeicosyl group, etc.

Examples of a $C_1$–$C_{20}$ aralkyl group for $R^1$, $R^2$, $R^3$, $R^4$, $R^5$ or $R^6$ include a benzyl group, a (2-methylphenyl)methyl group, a (3-methylphenyl)methyl group, a (4-methylphenyl)

methyl group, a (2,3-dimethylphenyl)methyl group, a (2,4-dimethylphenyl)methyl group, a (2,5-dimethylphenyl) methyl group, a (2,6-dimethylphenyl)methyl group, a (3,4-dimethylphenyl)methyl group, a (4,6-dimethylphenyl) methyl group, a (2,3,4-trimethylphenyl)methyl group, a (2,3,5-trimethylphenyl)methyl group, a (2,3,6-trimethylphenyl)methyl group, a (3,4,5-trimethylphenyl) methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isoproyplphenyl)methyl group, a (n-butylphenyl) methyl group, a (sec.-butylphenyl)methyl group, a (tert.-butylphenyl)methyl group, a (n-pentylphenyl)methyl group, a (neopentylphenyl)methyl group, a (n-hexylphenyl)methyl group, a (n-octylphenyl)methyl group, a (n-decylphenyl) methyl group, a (n-tetradecylphenyl)methyl group, a naphthylmethyl group, an anthracenylmethyl group, etc. Among them, a benzyl group is preferable. Any one of these aralkyl groups may optionally be substituted by one or more fluorine atoms.

Examples of a $C_6$–$C_{20}$ aryl group for $R^1$, $R^2$, $R^3$, $R^4$, $R^5$ or $R^6$ include a phenyl group, a a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, a isopropylphenyl group, a n-butylphenyl group, a sec.-butylphenyl group, a tert.-butylphenyl group, a n-pentylphenyl group, a neopentylphenyl group, a n-hexylphenyl group, a n-octylphenyl group, a n-decylphenyl group, a n-dodecylphenyl group, a tetradecylphenyl group, a naphthyl group, an anthracenyl group, etc. Among them, a phenyl group is preferable. Any one of these aryl groups may optionally be substituted by one or more fluorine atoms.

A substituted silyl group for $R^1$, $R^2$, $R^3$, $R^4$, $R^5$ or $R^6$ means a silyl group which is substituted by one or more hydrocarbon groups. Here, examples of hydrocarbon groups include $C_1$–$C_{10}$ hydrocarbon groups such as a methyl group, an ethyl group, a n-propyl group, an isopropyl group, a n-butyl group, a sec.-butyl group, a tert.-butyl group, an isobutyl group, a n-pentyl group, a n-hexyl group, a cyclohexyl group, etc.; aryl groups such as a phenyl group, etc. Examples of a $C_1$–$C_{20}$ substituted silyl group include mono-substituted silyl groups having 1 to 20 carbon atoms such as a methylsilyl group, an ethylsilyl group, a phenylsilyl group, etc.; di-substituted silyl groups having 2 to 20 carbon atoms such as a dimethylsilyl group, a diethylsilyl group, a diphenylsilyl group, etc.; tri-substituted silyl groups having 3 to 20 carbon atoms such as a trimethylsilyl group, a triethylsilyl group, a tri-n-propylsilyl group, a triisopropylsilyl group, a tri-n-butylsilyl group, a tri-sec.-butylsilyl group, a tri-tert.-butylsilyl group, a triisobutylsilyl group, a tert.-butyldimethylsilyl group, a tri-n-pentylsilyl group, a tri-n-hexylsilyl group, a tricyclohexylsilyl group, a triphenylsilyl group, etc. Among them, a trimethylsilyl group, a tert.-butyldimethylsilyl group and a triphenylsilyl group are preferable. Any one of the hydrocarbon groups of these substituted silyl groups may optionally be substituted by one or more fluorine atoms.

Examples of a $C_1$–$C_{20}$ alkoxyl group for $R^1$, $R^2$, $R^3$, $R^4$, $R^5$ or $R^6$ include a methoxy group, an ethoxy group, a n-propoxy group, an isopropoxy group, a n-butoxy group, a sec.-butoxy group, a tert.-butoxy group, a n-pentyloxy group, a neopentyloxy group, a n-hexyloxy group, a n-octyloxy group, a n-dodecyloxy group, a n-pentadecyloxy group, a n-eicocyloxy group, etc. Among them, a methoxy group, an ethoxy group and a tert.-butoxy group are preferable. Any one of these alkoxyl groups may optionally be substituted by one or more fluorine atoms.

Examples of a $C_7$–$C_{20}$ aralkyloxyl group for $R^1$, $R^2$, $R^3$, $R^4$, $R^5$ or $R^6$ include a benzyloxy group, a (2-methylphenyl) methoxy group, a (3-methylphenyl)methoxy group, a (4-methylphenyl)methoxy group, a (2,3-dimethylphenyl) methoxy group, a (2,4-dimethylphenyl)methoxy group, a (2,5-dimethylphenyl)methoxy group, a (2,6-dimethylphenyl)methoxy group, a (3,4-dimethylphenyl) methoxy group, a (3,5-dimethylphenyl)methoxy group, a (2,3,4-trimethylphenyl)methoxy group, a (2,3,5-trimethylphenyl)methoxy group, a (2,3,6-trimethylphenyl) methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl) methoxy group, an (ethylphenyl)methoxy group, a (n-propylphenyl)methoxy group, an (isopropylphenyl) methoxy group, a (n-butylphenyl)methoxy group, a (sec.-butylphenyl)methoxy group, a (tert.-butylphenyl)methoxy group, a (n-hexylphenyl)methoxy group, a (n-octylphenyl) methoxy group, a (n-decylphenyl)methoxy group, a (n-tetradecylphenyl)methoxy group, a naphthylmethoxy group, an anthracenylmethoxy group, etc. Among them a benzyloxy group is preferable. Any one of these aralkyloxyl groups may optionally be substituted by one or more fluorine atoms.

Examples of an aryloxyl group for $R^1$, $R^2$, $R^3$, $R^4$, $R^5$ or $R^6$ include $C_6$–$C_{20}$ aryloxyl groups such as a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec.-butylphenoxy group, a tert.-butylphenoxy group, a n-hexylphenoxy group, a n-octylphenoxy group, a n-decylphenoxy group, a n-tetradecylphenoxy group, a naphthoxy group, an anthracenyloxy group, etc. Any one of these aryloxyl groups may optionally be substituted by one or more fluorine atoms.

A $C_2$–$C_{20}$ disubstituted amino group for $R^1$, $R^2$, $R^3$, $R^4$, $R^5$ or $R^6$ means an amino group which is substituted by two hydrocarbon groups. Here, examples of hydrocarbon groups include $C_2$–$C_{20}$ hydrocarbon groups such as a methyl group, an ethyl group, a n-propyl group, an isopropyl group, a n-butyl group, a sec.-butyl group, a tert.-butyl group, an isobutyl group, a n-pentyl group, a n-hexyl group, a cyclohexyl group, etc.; aryl groups such as a phenyl group, etc. Examples of the $C_1$–$C_{10}$ disubstituted amino group include a dimethylamino group, a diethylamino group, a di-n-propylamino group, a diisopropylamino group, a di-n- butylamino group, a di-sec.-butylamino group, a di-tert.-butylamino group, a diisobutylamino group, a tert.-butylisopropylamino group, a di-n-hexylamino group, a di-n-octylamino group, a di-n-decylamino group, a diphenylamino group, a bistrimethylsilylamino group, a bis-tert.-butyldimethylsilylamino group, etc. Among them, a dimethylamino group and a diethylamino group are preferable. Any one of these disubstituted amino groups may optionally be substituted by one or more fluorine atoms.

Any two or more groups of $R^1$, $R^2$, $R^3$, $R^4$, $R^5$ and $R^6$ may optionally bond each other to form a ring or rings.

Examples of a hydrocarbon group for $R^7$ include $C_1$–$C_{10}$ alkyl groups such as a methyl group, an ethyl group, a propyl group, a hexyl group, a decyl group, etc.; $C_2$–$C_{10}$ alkenyl groups such as a vinyl group, an allyl group, a propenyl group, a 2-methyl-2-propenyl group, a homoallyl group, a hexenyl group, a decenyl group, etc.; alkoxyalkyl groups such as a methoxymethyl group, a methoxyethoxymethyl group, etc.; $C_7$–$C_{12}$ aralkyl groups such as a benzyl group, a (4-methylphenyl)methyl group, a (2,4,6-trimethylphenyl) methyl group, etc. Any one of these hydrocarbon groups may optionally be substituted by one or more halogen atoms. Examples of halogen-substituted hydrocarbon groups include a 2-chloro-2-propenyl group, and the like.

Examples of a tri-substituted silyl group include a trimethylsilyl group, a triethylsilyl group, a tri-n-propylsilyl group, a triisopropylsilyl group, a tri-n-butylsilyl group, a tri-sec.-butylsilyl group, a tri-tert.-butylsilyl group, a tri-isobutylsilyl group, a tert.-butyldimethylsilyl group, a tri-n-pentylsilyl group, a tri-n-hexylsilyl group, a tricyclohexylsilyl group, a triphenylsilyl group, etc.

Specific examples of the compound (1) in which B is a carbon atom include 2-bromo-2-(2-methoxyphenyl) propane, 2-bromo-2-(2-methoxy-3-methylphenyl)propane, 2-bromo-2-(2-methoxy-3,5-dimethylphenyl)propane, 2-bromo-2-(3-tert.-butyl- 2-methoxyphenyl)propane, 2-bromo-2-(3-tert.-butyl-2-methoxy-5-methylphenyl) propane, 2-bromo-2-(3,5-di-tert.-butyl-2-methoxyphenyl) propane, 2-bromo-2-(2-methoxy-3-phenylphenyl)propane, 2-bromo-2-(2-methoxy-5-methyl-3-phenylphenyl)propane, 2-bromo-2-(3-tert.-butyldimethylsilyl-2-methoxyphenyl) propane, 2-bromo-2-(3-tert.-butyldimethylsilyl-2-methoxy-5-methylphenyl)propane, 2-bromo-2-(2-methoxy-3-trimethylsilylphenyl)propane, 2-bromo-2-(2-methoxy-5-methyl-3-trimethylsilylphenyl)propane, 2-bromo-2-(3,5-diamyl-2-methoxyphenyl)propane, 2-bromo-2-(3-tert.-butyl-2,5-dimethoxyphenyl)propane, 2-bromo-2-(3-tert.-butyl-5-chloro-2-methoxyphenyl)propane, 2-bromo-2-(2-allyloxyphenyl)propane, 2-bromo-2-(2-allyloxy-3-methylphenyl)propane, 2-bromo-2-(2-allyloxy-3,5-dimethylphenyl)propane, 2-bromo-2-(2-allyloxy-3-tert.-butylphenyl)propane, 2-bromo-2-(2-allyloxy-3-tert.-butyl-5-methylphenyl)propane, 2-bromo-2-(2-allyloxy-3,5-di-tert.-butylphenyl)propane, 2-bromo-2-(2-allyloxy-3-phenylphenyl)propane, 2-bromo-2-(2-allyloxy-5-methyl-3-phenylphenyl)propane, 2-bromo-2-(2-allyloxy-3-tert.-butyldimethylsilylphenyl)propane, 2-bromo-2-(2-allyloxy-3-tert.-butyldimethylsilyl-4-methylphenyl)propane, 2-bromo-2-(2-allyloxy-3-trimethylsilylphenyl)propane, 2-bromo-2-(2-allyloxy-5-methyl-3-trimethylsilylphenyl) propane, 2-bromo-2-(2-allyloxy-3,5-diamylphenyl)propane, 2-bromo-2-(2-allyloxy-3-tert.-butyl-5-methoxyphenyl) propane, 2-bromo-2-(2-allyloxy-3-tert.-butyl-5-chlorophenyl)propane, 2-bromo-2-(1-allyloxynaphthalen-2-yl)propane, etc.

Examples of the compound (1) in which B is a carbon atom also include analogous compounds to the above exemplified compounds in which a methoxy or allyloxy group is replaced by a benzyloxy group, an ethoxy group, a trimethylsilyloxy group, a tert.-butyldimethylsilyloxy group or a methoxymethoxy group; or propane is replaced by methane, ethane, butane, pentane, hexane, phenylmethane or diphenylmethane; or a bromo moiety is replaced by an iodo moiety.

Examples of the compound (1) in which B is a silicon atom include chloro(2-methoxyphenyl)dimethylsilane, chloro(2-methoxy-3-methylphenyl)dimethylsilane, chloro (2-methoxy-3,5-dimethylphenyl)dimethylsilane, (3-tert.-butyl-2-methoxyphenyl)chlorodimethylsilane, (3-tert.-butyl-2-methoxy-5-methylphenyl)chlorodimethylsilane, (3,5-di-tert.-butyl-2-methoxyphenyl)chlorodimethylsilane, chloro(2-methoxy-3-phenylphenyl)dimethylsilane, chloro (2-methoxy-5-methyl-3-phenylphenyl)dimethylsilane, (3-tert.-butyldimethylsilyl-2-methoxyphenyl) chlorodimethylsilane, (3-tert.-butyldimethylsilyl-2-methoxy-5-methylphenyl)chlorodimethylsilane, chloro(2-methoxy-3-trimethylsilylphenyl)dimethylsilane, chloro(2-methoxy-5-methyl-3-trimethylsilylphenyl)dimethylsilane, (3,5-diamyl-2-methoxyphenyl)chlorodimethylsilane, (3-tert.-butyl-2,5-dimethoxyphenyl)chlorodimethylsilane, (3-tert.-butyl-5-chloro-2-methoxyphenyl) chlorodimethylsilane, (2-allyloxyphenyl) chlorodimethylsilane, (2-allyloxy-3-methylphenyl) chlorodimethylsilane, (2-allyloxy-3,5-dimethylphenyl) chlorodimethylsilane, (2-allyloxy-3-tert.-butylphenyl) chlorodimethylsilane, (2-allyloxy-3-tert.-butyl-5-methylphenyl)chlorodimethylsilane, (2-allyloxy-3,5-di-tert.-butylphenyl)chlorodimethylsilane, (2-allyloxy-3-phenylphenyl) chlorodimethylsilane, (2-allyloxy-5-methyl-3-phenylphenyl)chlorodimethylsilane, (2-allyloxy-3-tert.-butyldimethylsilylphenyl)chlorodimethylsilane, (2-allyloxy-3-tert.-butyldimethylsilyl-4-methylphenyl) chlorodimethylsilane, (2-allyloxy-3-trimethylsilylphenyl) chlorodimethylsilane, (2-allyloxy-5-methyl-3-trimethylsilylphenyl)chlorodimethylsilane, (2-allyloxy-3,5-diamylphenyl)chlorodimethylsilane, (2-allyloxy-3-tert.-butyl-5-methoxyphenyl)chlorodimethylsilane, (2-allyloxy-3-tert.-butyl-5-chlorophenyl)chlorodimethylsilane, (1-allyloxynaphthalen-2-yl)chlorodimethylsilane, etc.

Examples of the compound (1) in which B is a silicon atom also include analogous compounds to the above exemplified compounds in which a methocy group or an allyloxy group is replaced by a benzyloxy group, an ethoxy group, a trimethylsilyloxy group, a tert.-butyldimethylsilyloxy group or a methoxymethoxy group; or a chlorodimethylsilane group is replaced by a chlorodiethylsilane group, a chlorodiphenylsilane group, chlorodimethoxysilane group, a bromodimethylsilane group or a dimethyliodosilane group.

The compound (2) may be any compound having a cylopentadineyl moiety. Examples of the compound (2) may be the same as those exemplified for the compound (2a).

Examples of an amine compound may be the same as those used in the process according to the first asepct of the present invention.

The reaction is usually carried out in a solvent which is inactive to the reaction. Examples of such solvents are aprotic solvents, for example, aromatic hydrocarbon solvents such as benzene, toluene, xylene, etc.; aliphatic hydrocarbon solvents such as pentane, hexane, heptane, octane, cyclohexane, etc.; ether solvents such as diethyl ether, methyl tert.-butyl ether, tetrahydrofuran, 1,4-dioxane, etc.; amide solvents such as hexamethylphosphoric amide, dimethylformamide, dimethylacetamide, N-methylpyrrolidone, etc.; halogen-containing solvents such as chlorobenzene, dichlorobenzene, etc. These solvents may be used singly or in admixture of two or more solvents. The amount of a solvent is usually from 1 to 200 wt. parts, preferably from 3 to 30 wt. parts, per 1 wt. part of a cyclopentadiene.

This reaction is usually carried out by mixing a metal hydride, an amine compound and the compound (2) in a solvent, and then adding the compound (1), although the desired compound (3) can be synthesized by mixing all the compounds at the same time.

A reaction temperature is not limited, but is preferably in a range in which no low-temperature facilities are necessary, for the industrial production. For example, a reaction temperature is usually in the range between 0 and 70° C., preferably between 10 and 60° C.

The amount of the compound (2) is usually in the range between 0.5 and 5 moles, preferably between 0.8 and 3 moles, per one mole of the compound (1).

Examples of metal hydrides include alkali metal hydrides such as lithium hydride, sodium hydride, potassium hydride, etc.; and alkaline earth metal hydrides such as calcium hydride, etc. The amount of a metal hydride is usually from 0.5 to 3 moles, preferably from 0.9 to 2.0 moles, per one mole of the compound (2). Sodium hydride and potassium hydride can be used in the form of a marketed product containing mineral oils, although they may be used after washing the mineral oils off with hydrocarbon solvents such as hexane, etc.

The amount of an amine compound is usually from 0.001 to 2 moles, preferably from 0.01 to 0.5 mole, per one mole of a metal hydride.

After the completion of the reaction, water, or an acidic aqueous solution such as the aqueous solution of ammonium chloride or hydrochloric acid is added to the reaction mixture. Then, the mixture was separated to an organic phase and an aqueous phase, and the solution of the compound (3) is recovered in the form of the organic phase.

When a solvent miscible with water is used in the reaction or when a reaction mixture cannot be separated to an organic phase and an aqueous phase since the amount of a solvent used in the reaction is low, an organic solvent, which is insoluble in water such as toluene, ethyl acetate, chlorobenzene and the like, can be added to the reaction mixture, and then the reaction mixture is separated to an organic phase and an aqueous phase.

The compound (3) can be isolated from the organic phase by concentration. If desired, the compound (3) can be purified by distillation, column chromatography, etc.

In the obtained compound (3), examples of a group having a cyclopentadiene moiety, which is represented by Cp, may be the groups exemplified for the compound (2a). In particular, examples of such a group include a $\eta^5$-cyclopentadienyl group, a $\eta^5$-methylcyclopentadienyl group, a $\eta^5$-dimethylcyclopentadienyl group, a $\eta^5$-trimethylcyclopentadienyl group, a $\eta^5$-tetramethylcyclopentadienyl group, a $\eta^5$-ethylcyclopentadienyl group, a $\eta^5$-n-propylcyclopentadienyl group, a $\eta^5$-isopropylcyclopentadienyl group, a $\eta^5$-n-butylcyclopentadienyl group, a $\eta^5$-sec.-butylcyclopentadienyl group, a $\eta^5$-tert.-butylcyclopentadienyl group, a $\eta^5$-n-pentylcyclopentadienyl group, a $\eta^5$-neopentylcyclopentadienyl group, a $\eta^5$-n-hexylcyclopentadienyl group, a $\eta^5$-n-octylcyclopentadienyl group, a $\eta^5$-phenylcyclopentadienyl group, a $\eta^5$-naphthylcyclopentadienyl group, a $\eta^5$-trimethylsilylcyclopentadienyl group, a $\eta^5$-triethylsilylcyclopentadienyl group, a $\eta^5$-tert.-butyldimethylsilylcyclopentadienyl group, a $\eta^5$-indenyl group, a $\eta^5$-methylindenyl group, a $\eta^5$-dimethylindenyl group, a $\eta^5$-ethylindenyl group, a $\eta^5$-n-propylindenyl group, a $\eta^5$-isopropylindenyl group, a $\eta^5$-n-butylindenyl group, a $\eta^5$-sec.-butylindenyl group, a $\eta^5$-tert.-butylindenyl group, a $\eta^5$-n-pentylindenyl group, a $\eta^5$-neopentylindenyl group, a $\eta^5$n-hexylindenyl group, a $\eta^5$-n-octylindenyl group, a $\eta^5$-n-decylindenyl group, a $\eta^5$-phenylindenyl group, a $\eta^5$-methylphenylindenyl group, a $\eta^5$-naphthylindenyl group, a $\eta^5$-trimethylsilylindenyl group, a $\eta^5$-triethylsilylindenyl group, a $\eta^5$-tert.-butyldimethylsilylindenyl group, a $\eta^5$-tetrahydroindenyl group, a $\eta^5$-fluorenyl group, a $\eta^5$-methylfluorenyl group, a $\eta^5$-dimethylfluorenyl group, a $\eta^5$-ethylfluorenyl group, a $\eta^5$-diethylfluorenyl group, a $\eta^5$-n-propylfluorenyl group, a $\eta^5$-di-n-propylfluorenyl group, a $\eta^5$-isopropylfluorenyl group, a $\eta^5$-diisoproylfluorenyl group, a $\eta^5$-n-butylfluorenyl group, a $\eta^5$-sec.-butylfluorenyl group, a $\eta^5$-tert.-butylfluorenyl group, a $\eta^5$-di-n-butylfluorenyl group, a $\eta^5$-di-sec.-butylfluorenyl group, a $\eta^5$-di-tert.-butylfluorenyl group, a $\eta^5$-n-pentylfluorenyl group, a $\eta^5$-neopentylfluorenyl group, a $\eta^5$-n-hexylfluorenyl group, a $\eta^5$-n-octylfluorenyl group, a $\eta^5$-n-decylfluorenyl group, a $\eta^5$-n-dodecylfluorenyl group, a $\eta^5$-phenylfluorenyl group, a $\eta^5$-diphenylfluorenyl group, a $\eta^5$-methylphenylfluorenyl group, a $\eta^5$-naphthylfluorenyl group, a $\eta^5$-trimethylsilylfluorenyl group, a $\eta^5$-bis-trimethylsilylfluorenyl group, a $\eta^5$-triethylsilylfluorenyl group, a $\eta^5$-tert.-butyldimethylsilylfluorenyl group, etc.

Specific examples of the cyclopentadiene derivative (3) include 2-[(cyclopenta-1,4-dienyl)methyl]-1-methoxybenzene, 2-[(cyclopenta-1,4-dienyl)methyl]-1-methoxy-4,6-dimethylbenzene, 2-tert.-butyl-6-[(cyclopenta-1,4-dienyl)methyl]-1-methoxy-4-methylbenzene, 6-[(cyclopenta-1,4-dienyl)methyl]-1-methoxy-2-phenylbenzene, 1-tert.-butyldimethylsilyl-3-[(cyclopenta-1,4-dienyl)methyl]-2-methoxy-5-methylbenzene, 3-[(cyclopenta-1,4-dienyl)methyl]-2-methoxy-5-methyl-1-trimethylsilylbenzene, 2-tert.-butyl-6-[(cyclopenta-1,4-dienyl)methyl]-1,4-dimethoxybenzene, 3-tert.-butyl-1-chloro-5-[(cyclopenta-1,4-dienyl)methyl]-4-methoxybenzene, 2-tert.-butyl-6-[(cyclopenta-1,4-dienyl)methyl]-1-methoxybenzene, 2-[1-(cyclopenta-1,4-dienyl)-1-methylethyl]-1-methoxybenzene, 2-[1-(cyclopenta-1,4-dienyl)-1-methylethyl]-1-methoxy-4,6-dimethylbenzene, 6-tert.-butyl-2-[1-(cyclopenta-1,4-dienyl)-1-methylethyl]-1-methoxy-4-methylbenzene, 6-[1-(cyclopenta-1,4-dienyl)-1-methylethyl]-1-methoxy-2-phenylbenzene, 1-tert.-butyldimethylsilyl-3-[1-(cyclopenta-1,4-dienyl)-1-methylethyl]-2-methoxy-5-methylbenzene, 3-[1-(cyclopenta-1,4-dienyl)-1-methylethyl]-2-methoxy-5-methyl-1-trimethylsilylbenzene, 6-tert.-butyl-2-[1-(cyclopenta-1,4-dienyl)-1-methylethyl]-1,4-dimethoxybenzene, 5-tert.-butyl-1-chloro-3-[1-cyclopenta-1,4-dienyl)-1-methylethyl]-4-methoxybenzene, 6-tert.-butyl-2-[1-cyclopenta-1,4-dienyl)-1-methylethyl]-1-methoxybenzene, 1-methoxy-2-[1-(4-methylcyclopenta-1,4-dienyl)-1-methylethyl]benzene, 1-methoxy-4,6-dimethyl-2-[1-(4-methylcyclopenta-1,4-dienyl)-1-methylethyl]benzene, 6-tert.-butyl-1-methoxy-4-methyl-2-[1-(4-methylcyclopenta-1,4-dienyl)-1-methylethyl]benzene, 1-methoxy-6-[1-(4-methylcyclopenta-1,4-dienyl)-1-methylethyl]-2-phenylbenzene, 1-tert.-butyldimethylsilyl-2-methoxy-5-methyl-3-[1-(4-methylcyclopenta-1,4-dienyl)-1-methylethyl]benzene, 2-methoxy-5-methyl- 3-[1-(4-methylcyclopenta-1,4-dienyl)-1-methylethyl]-1- trimethylsilylbenzene, 6-tert.-butyl-1,4-dimethoxy-2-[1-(4-methylcyclopenta-1,4-dienyl)-1-methylethyl]benzene, 5-tert.-butyl-1-chloro-4-methoxy-3-[1-(4-methylcyclopenta-1,4-dienyl)-1-methylethyl]benzene, 6-tert.-butyl-1-methoxy-2-[1-(4-methylcyclopenta-1,4-dienyl)-1-methylethyl]benzene, 2-[1-(4-tert.-butylcyclopenta-1,4-dienyl)-1-methylethyl]-1-methoxybenzene, 2-[1-(4-tert.-butylcyclopenta-1,4-dienyl)-1-methylethyl]-1-methoxy-4,6-dimethylbenzene, 6-tert.-butyl-2-[1-(4-tert.-butylcyclopenta-1,4-dienyl)-1-methylethyl]-1-methoxy-4-methylbenzene, 6-[1-(4-tert.-butylcyclopenta-1,4-dienyl)-1-methylethyl]-1-methoxy-2-phenylbenzene, 1-tert.-butyldimethylsilyl-3-[1-(4-tert.-butylcyclopenta-1,4-dienyl)-1-methylethyl]-2-methoxy-5-methylbenzene, 3-[1-(4-tert.-butylcyclopenta-1,4-dienyl)-1-methylethyl]-2-methoxy-5-methyl-1-trimethylsilylbenzene, 6-tert.-butyl-2-[1-(4-tert.-butylcyclopenta-1,4-dienyl)-1-methylethyl]-1,4-dimethoxybenzene, 5-tert.-butyl-1-chloro-3-[1-(4-tert.-butylcyclopenta-1,4-dienyl)-1-methylethyl]-4-methoxybenzene, 6-tert.-butyl-2-[1-(4-tert.-butylcyclopenta-1,4-dienyl)-1-methylethyl]-1-methoxybenzene, 1-methoxy-2-[1-(2,3,4,5-tetramethylcyclopenta-1,4-dienyl)-1-methylethyl]benzene, 1-methoxy-4,6-dimethyl-2-[1-(2,3,4,5-tetramethylcyclopenta-1,4-dienyl)-1-methylethyl]benzene, 6-tert.-butyl-1-methoxy-4-methyl-2-[1-(2,3,4,5-tetramethylcyclopenta-1,4-dienyl)-1-methylethyl]benzene, 1-methoxy-2-phenyl-6-[1-(2,3,4,5-tetramethylcyclopenta-1,4-dienyl)-1-methylethyl]benzene, 1-tert.-butyldimethylsilyl-2-methoxy-5-methyl-3-[1-(2,3,4,5-tetramethylcyclopenta-1,4-dienyl)-1-methylethyl]benzene, 2-methoxy-5-methyl-3-[1-(2,3,4,5-tetramethylcyclopenta-1,4-dienyl)-1-methylethyl]-1-trimethylsilylbenzene, 6-tert.-butyl-1,4-dimethoxy-2-[1-(2,3,4,5-tetramethylcyclopenta-1,4-dienyl)-1-methylethyl]benzene, 5-tert.-butyl-1-chloro-4-methoxy-3-[1-(2,3,4,5-tetramethylcyclopenta-1,4-dienyl)-1-methylethyl]benzene, 6-tert.-butyl-1-methoxy-2-[1-(2,3,4,5-tetramethylcyclopenta-1,4-dienyl)-1-methylethyl]benzene, 1-methoxy-2-[1-(3-trimethylsilylcyclopenta-1,4-dienyl)-1-methylethyl]benzene, 1-methoxy-4,6-dimethyl-2-[1-(3-trimethylsilylcyclopenta-1,4-dienyl)-1-methylethyl]benzene, 6-tert.-butyl-1-methoxy-4-methyl-2-[1-(3-trimethylsilylcyclopenta-1,4-dienyl)-1-methylethyl]benzene, 1-methoxy-2-phenyl-6-[1-(3-trimethylsilylcyclopenta-1,4-dienyl)-1-methylethyl]benzene, 1-tert.-butyldimethylsilyl-2-methoxy-5-methyl-3-[1-(3-trimethylsilylcyclopenta-1,4-dienyl)-1-methylethyl]benzene, 2-methoxy-5-methyl-1-trimethylsilyl-3-[1-(3-trimethylsilylcyclopenta-1,4-dienyl)-1-methylethyl]benzene, 6-tert.-butyl-1,4-dimethoxy-2-[1-(3-trimethylsilylcyclopenta-1,4-dienyl)-1-methylethyl]benzene, 5-tert.-butyl-1-chloro-4-methoxy-3-[1-(3-trimethylsilylcyclopenta-1,4-dienyl)-1-methylethyl]benzene, 6-tert.-butyl-1-methoxy-2-[1-(3-trimethylsilylcyclopenta-1,4-dienyl)-1-methylethyl]benzene, 2-[1-(cyclopenta-1,4-dienyl)-1-ethylpropyl]-1-methoxybenzene, 2-[1-(cyclopenta-1,4-dienyl)-1-ethylpropyl]-1-methoxy-4,6-dimethylbenzene, 6-tert.-butyl-2-[1-(cyclopenta-1,4-dienyl)-1-ethylpropyl]-1-methoxy-4-methylbenzene, 6-[1-(cyclopenta-1,4-dienyl)-1-ethylpropyl]-1-methoxy-2-phenylbenzene, 1-tert.-butyldimethylsilyl-3-[1-(cyclopenta-1,4-dienyl)-1-ethylpropyl]-2-methoxy-5-methylbenzene, 3-[1-(cyclopenta-1,4-dienyl)-1-ethylpropyl]-2-methoxy-5-methyl-1-trimethylsilylbenzene, 6-tert.-butyl-2-[1-(cyclopenta-1,4-dienyl)-1-ethylpropyl]-1,4-dimethoxybenzene, 5-tert.-butyl-1-chloro-3-[1-(cyclopenta-1,4-dienyl)-1-ethylpropyl]-4-methoxybenzene, 6-tert.-butyl-2-[1-(cyclopenta-1,4-dienyl)-1-ethylpropyl]-1-methoxybenzene, 2-[1-(cyclopenta-1,4-dienyl)-1,1-diphenylmethyl]-1-methoxybenzene, 2-[1-(cyclopenta-1,4-dienyl)-1,1-diphenylmethyl]-1-methoxy-4,6-dimethylbenzene, 6-tert.-butyl-2-[1-(cyclopenta-1,4-dienyl)-1,1-diphenylmethyl]-1-methoxy-4-methylbenzene, 2-[1-cyclopenta-1,4-dienyl)-1,1-diphenylmethyl]-1-methoxy-6-phenylbenzene, 1-tert.-butyldimethylsilyl-3-[1-(cyclopenta-1,4-dienyl)-1,1-diphenylmethyl]-2-methoxy-5-methylbenzene, 3-[(cyclopenta-1,4-dienyl)-1,1-diphenylmethyl]-2-methoxy-5-methyl-1-trimethylsilylbenzene, 6-tert.-butyl-2-[(cyclopenta-1,4-dienyl)-1,1-diphenylmethyl]-1,4-dimethoxybenzene, 5-tert.-butyl-1-chloro-3-[(cyclopenta-1,4-dienyl)-1,1-diphenylmethyl]-4-methoxybenzene, 6-tert.-butyl-2-[(cyclopenta-1,4-dienyl)-1,1-diphenylmethyl]-1-methoxybenzene, 1-allyloxy-2-[(cyclopenta-1,4-dienyl)methyl]benzene, 1-allyloxy-2-[(cyclopenta-1,4-dienyl)methyl]-4,6-dimethylbenzene, 1-allyloxy-2-tert.-butyl-6-[(cyclopenta-1,4-dienyl)methyl]-4-methylbenzene, 1-allyloxy-6-[(cyclopenta-1,4-dienyl)methyl]-2-phenylbenzene, 2-allyloxy-1-tert.-butyldimethylsilyl-3-[(cyclopenta-1,4-dienyl)methyl]-5-methylbenzene, 2-allyloxy-3-[(cyclopenta-1,4-dienyl)methyl]-5-methyl-1-trimethylsilylbenzene, 1-allyloxy-2-tert.-butyl-6-[(cyclopenta-1,4-dienyl)methyl]-4-methoxybenzene, 4-allyloxy-3-tert.-butyl-1-chloro-5-[(cyclopenta-1,4-dienyl)methyl]benzene, 1-allyloxy-2-tert.-butyl-6-[(cyclopenta-1,4-dienyl)methyl]benzene, 1-allyloxy-2-[1-(cyclopenta-1,4-dienyl)-1-methylethyl]benzene, 1-allyloxy-2-[1-(cyclopenta-1,4-dienyl)-1-methylethyl]-4,6-dimethylbenzene, 1-allyloxy-6-tert.-butyl-2-[1-(cyclopenta-1,4-dienyl)-1-methylethyl]-4-methylbenzene, 1-allyloxy-6-[1-(cyclopenta-1,4-dienyl)-1-methylethyl]-2-phenylbenzene, 2-allyloxy-1-tert.-butyldimethylsilyl-3-[1-(cyclopenta-1,4-dienyl)-1-methylethyl]-5-methylbenzene, 2-allyloxy-3-[1-(cyclopenta-1,4-dienyl)-1-methylethyl]-5-methyl-1-trimethylsilylbenzene, 1-allyloxy-6-tert.-butyl-2-[1-(cyclopenta-1,4-dienyl)-1-methylethyl]-4-methoxybenzene, 4-allyloxy-5-tert.-butyl-1-chloro-3-[1-(cyclopenta-1,4-dienyl)-1-methylethyl]benzene, 1-allyloxy-6-tert.-butyl-2-[1-(cyclopenta-1,4-dienyl)-1-methylethyl]benzene, 1-allyloxy-2-[1-(4-methylcyclopenta-1,4-dienyl)-1-methylethyl]benzene, 1-allyloxy-4,6-dimethyl-2-[1-(4-methylcyclopenta-1,4-dienyl)-1-methylethyl]benzene, 1-allyloxy-6-tert.-butyl-4-methyl-2-[1-(4-methylcyclopenta-1,4-dienyl)-1-methylethyl]benzene, 1-allyloxy-6-[1-(4-methylcyclopenta-1,4-dienyl)-1-methylethyl]-2-phenylbenzene, 2-allyloxy-1-tert.-butyldimethylsilyl-5-methyl-3-[1-(4-methylcyclopenta-1,4-dienyl)-1-methylethyl]benzene, 2-allyloxy-5-methyl-3-[1-(4-methylcyclopenta-1,4-dienyl)-1-methylethyl]-1-trimethylsilylbenzene, 1-allyloxy-6-tert.-butyl-4-methoxy-2-[1-(4-methylcyclopenta-1,4-dienyl)-1-methylethyl]benzene, 4-allyloxy-5-tert.-butyl-1-chloro-3-[1-(4-methylcyclopenta-1,4-dienyl)-1-methylethyl]benzene, 1-allyloxy-6-tert.-butyl-2-[1-(4-methylcyclopenta-1,4-dienyl)-1-methylethyl]benzene, 1-allyloxy-2-[1-(4-tert.-butylcyclopenta-1,4-dienyl)-1-methylethyl]benzene, 1-allyloxy-2-[1-(4-tert.-butylcyclopenta-1,4-dienyl)-1-methylethyl]-4,6-dimethylbenzene, 1-allyloxy-6-tert.-butyl-2-[1-(4-tert.-butylcyclopenta-1,4-dienyl)-1-methylethyl]-4-methylbenzene, 1-allyloxy-6-[1-(4-tert.-butylcyclopenta-1,4-dienyl)-1-methylethyl]-2-phenylbenzene, 2-allyloxy-1-tert.-butyldimethylsilyl-3-[1-(4-tert.-butylcyclopenta-1,4- dienyl)-1-methylethyl]-5-methylbenzene, 2-allyloxy-3-[1-(4-tert.-butylcyclopenta-1,4-dienyl)-1-methylethyl]-5-methyl-1-trimethylsilylbenzene, 1-allyloxy-6-tert.-butyl-2-[1-(4-tert.-butylcyclopenta-1,4-dienyl)-1-methylethyl]-4-methoxybenzene, 4-allyloxy-5-tert.-butyl-1-chloro-3-[1-(4-tert.-butylcyclopenta-1,4-dienyl)-1-methylethyl]benzene, 1-allyloxy-6-tert.-butyl-2-[1-(4-tert.-butylcyclopenta-1,4-dienyl)-1-methylethyl]benzene, 1-allyloxy-2-[1-(2,3,4,5-tetramethylcyclopenta-1,4-dienyl)-1-methylethyl]benzene, 1-allyloxy-4,6-dimethyl-2-[1-(2,3,4,5-tetramethylcyclopenta-1,4-dienyl)-1-methylethyl]benzene, 1-allyloxy-6-tert.-butyl-4-methyl-2-[1-(2,3,4,5-tetramethylcyclopenta-1,4-dienyl)-1-methylethyl]benzene, 1-allyloxy-2-phenyl-6-[1-(2,3,4,5-tetramethylcyclopenta-1,4-dienyl)-1-methylethyl]benzene, 2-allyloxy-1-tert.-butyldimethylsilyl-5-methyl-3-[1-(2,3,4,5-tetramethylcyclopenta-1,4-dienyl)-1-methylethyl]benzene, 2-allyloxy-5-methyl-3-[1-(2,3,4,5-tetramethylcyclopenta-1,4-dienyl)-1-methylethyl]-1-trimethylsilylbenzene, 1-allyloxy-6-tert.-butyl-4-methoxy-2-[1-(2,3,4,5-tetramethylcyclopenta-1,4-dienyl)-1-methylethyl]benzene, 4-allyloxy-5-tert.-butyl-1-chloro-3-[1-(2,3,4,5-tetramethylcyclopenta-1,4-dienyl)-1-methylethyl]benzene, 1-allyloxy-6-tert.-butyl-2-[1-(2,3,4,5-tetramethylcyclopenta-1,4-dienyl)-1-methylethyl]benzene, 1-allyloxy-2-[1-(3-trimethylsilylcyclopenta-1,4-dienyl)-1-methylethyl]benzene, 1-allyloxy-4,6-dimethyl-2-[1-(3-trimethylsilylcyclopenta-1,4-dienyl)-1-methylethyl]benzene, 1-allyloxy-6-tert.-butyl-4-methyl-2-[1-(3-trimethylsilylcyclopenta-1,4-dienyl)-1-methylethyl]benzene, 1-allyloxy-2-phenyl-6-[1-(3-trimethylsilylcyclopenta-1,4-dienyl)-1-methylethyl]benzene, 2-allyloxy-1-tert.-butyldimethylsilyl-5-methyl-3-[1-(3-trimethylsilylcyclopenta-1,4-dienyl)-1-methylethyl]benzene, 2-allyloxy-5-methyl-1-trimethylsilyl-3-[1-(3-trimethylsilylcyclopenta-1,4-dienyl)-1-methylethyl]benzene, 1-allyloxy-6-tert.-butyl-4-methoxy-2-[1-(3-trimethylsilylcyclopenta-1,4-dienyl)-1-methylethyl]benzene, 4-allyloxy-5-tert.-butyl-1-chloro-3-[1-(3-trimethylsilylcyclopenta-1,4-dienyl)-1-methylethyl]benzene, 1-allyloxy-6-tert.-butyl-2-[1-(3-trimethylsilylcyclopenta-1,4-dienyl)-1-methylethyl]benzene, 1-allyloxy-2-[1-(cyclopenta-1,4-dienyl)-1-ethylpropyl]benzene, 1-allyloxy-2-[1-(cyclopenta-1,4-dienyl)-1-ethylpropyl]-4,6-dimethylbenzene, 1-allyloxy-6-tert.-butyl-2-[1-(cyclopenta-1,4-dienyl)-1-ethylpropyl]-4-methylbenzene, 1-allyloxy-6-[1-(cyclopenta-1,4-dienyl)-1-ethylpropyl]-2-phenylbenzene, 2-allyloxy-1-tert.-butyldimethylsilyl-3-[1-(cyclopenta-1,4-dienyl)-1-ethylpropyl]-5-methylbenzene, 2-allyloxy-3-[1-(cyclopenta-1,4-dienyl)-1-ethylpropyl]-5-methyl-1-trimethylsilylbenzene, 1-allyloxy-6-tert.-butyl-2-[1-(cyclopenta-1,4-dienyl)-1-ethylpropyl]-4-methoxybenzene, 4-allyloxy-5-tert.-butyl-1-chloro-3-[1-(cyclopenta-1,4-dienyl)-1-ethylpropyl]benzene, 1-allyloxy-6-tert.-butyl-2-[1-(cyclopenta-1,4-dienyl)-1-ethylpropyl]benzene, 1-allyloxy-2-[1-(cyclopenta-1,4-dienyl)-1,1-diphenylmethyl]benzene, 1-allyloxy-2-[1-(cyclopenta-1,4-dienyl)-1,1-diphenylmethyl]-4,6-dimethylbenzene, 1-allyloxy-6-tert.-butyl-2-[1-(cyclopenta-1,4-dienyl)-1,1-diphenylmethyl]-4-methylbenzene, 1-allyloxy-2-[1-(cyclopenta-1,4-dienyl)-1,1-diphenylmethyl]-6-phenylbenzene, 2-allyloxy-1-tert.-butyldimethylsilyl-3-[1-(cyclopenta-1,4-dienyl)-1,1-diphenylmethyl]-5-methylbenzene, 2-allyloxy-3-[(cyclopenta-1,4-dienyl)-1,1-diphenylmethyl]-5-methyl-1-trimethylsilylbenzene, 1-allyloxy-6-tert.-butyl-2-[(cyclopenta-1,4-dienyl)-1,1-diphenylmethyl]-4-methoxybenzene, 4-allyloxy-5-tert.-butyl-1-chloro-3-[(cyclopenta-1,4-dienyl)-1,1-diphenylmethyl]benzene, 1-allyloxy-6-tert.-butyl-2-[(cyclopenta-1,4-dienyl)-1,1-diphenylmethyl]benzene, and analogous compounds to the above compounds in which a methoxy or an allyloxy group is replaced by an ethoxy group, a benzyloxy group, a trimethylsilyloxy group, a tert.-butyldimethylsilyloxy group or a methoxymethoxy group; or a cyclopenta-1,4-dienyl group is replaced by a dimethylcyclopenta-1,4-dienyl group, a trimethylcyclopenta-1,4-dienyl group, a n-butylcyclopenta-1,4-dienyl group, a tert.-butyldimethylsilylcyclopenta-1,4-dienyl group, an indenyl group or a fluorenyl group; or a 1-methoxybenzene group is replaced by a 1-methoxy-6-methylbenzene group, 1-methoxy-4,6-di-tert.-butylbenzene group, a 1-methoxy-4-methyl-6-phenylbenzene group, a 1-tert.-butyldimethylsilyl-2-methoxybenzene group or a 2-methoxy-1-trimethylsilylbenzene group; and further, (cyclopenta-1,3-dienyl)(2-methoxyphenyl)dimethylsilane (cyclopenta-1,3-dienyl) (2-methoxy-3-methylphenyl) dimethylsilane, (cyclopenta-1,3-dienyl)(2-methoxy-3,5-dimethylphenyl)dimethylsilane, (3-tert.-butyl-2-methoxyphenyl)(cyclopenta-1,3-dienyl)dimethylsilane, (3-tert.-butyl-2-methoxy-5-methylphenyl)(cyclopenta-1,3-dienyl)dimethylsilane, (3,5-di-tert.-butyl-2-methoxyphenyl)(cyclopenta-1,3-dienyl)dimethylsilane, (cyclopenta-1,3-dienyl)(2-methoxy-5-methyl-3-phenylphenyl)dimethylsilane, (cyclopenta-1,3-dienyl)(2-methoxy-5-methyl-3-trimethylsilylphenyl)dimethylsilane, (3-tert.-butyldimethylsilyl-2-methoxy-5-methylphenyl)(cyclopenta-1,3-dienyl)dimethylsilane, (3,5-diamyl-2-methoxyphenyl)(cyclopenta-1,3-dienyl)dimethylsilane, (3-tert.-butyl-2,5-dimethoxyphenyl)(cyclopenta-1,3-dienyl)dimethylsilane, (5-tert.-butyl-3-chloro-6-methoxyphenyl)(cyclopenta-1,3-dienyl)dimethylsilane, (2-methoxyphenyl)(methylcyclopenta-1,3-dienyl)dimethylsilane, (2-methoxy-3-methylphenyl)(methylcyclopenta-1,3-dienyl)dimethylsilane, (2-methoxy-3,5-dimethylphenyl)(methylcyclopenta-1,3-dienyl)dimethylsilane, (3-tert.-butyl-2-methoxyphenyl)(methylcyclopenta-1,3-dienyl)dimethylsilane, (3-tert.-butyl-2-methoxy-5-methylphenyl)(methylcyclopenta-1,3-dienyl)dimethylsilane, (3,5-di-tert.-butyl-2-methoxyphenyl)(methylcyclopenta-1,3-dienyl)dimethylsilane, (2-methoxy-5-methyl-3-phenylphenyl)(methylcyclopenta-1,3-dienyl)dimethylsilane, (2-methoxy-5-methyl-3-trimethylsilylphenyl)(methylcyclopenta-1,3-dienyl)dimethylsilane, (3-tert.-butyldimethylsilyl-2-methoxy-5-methylphenyl)(methylcyclopenta-1,3-dienyl)dimethylsilane, (3,5-diamyl-2-methoxyphenyl)(methylcyclopenta-1,3-dienyl)dimethylsilane, (3-tert.-butyl-2,5-dimethoxyphenyl)(methylcyclopenta-1,3-dienyl)dimethylsilane, (5-tert.-butyl-3-chloro-6-methoxyphenyl)(methylcyclopenta-1,3-dienyl)dimethylsilane, (2-methoxyphenyl)(2,3,4,5-tetramethylcyclopenta-1,3-dienyl)dimethylsilane, (2-methoxy-3-methylphenyl)(2,3,4,5-tetramethylcyclopenta-1,3-dienyl)dimethylsilane, (2-methoxy-3,5-dimethylphenyl)(2,3,4,5-tetramethylcyclopenta-1,3-dienyl)dimethylsilane, (3-tert.-butyl-2-methoxyphenyl)(2,3,4,5-tetramethylcyclopenta-1,3-dienyl)dimethylsilane, (3-tert.-butyl-2-methoxy-5-methylphenyl)(2,3,4,5-tetramethylcyclopenta-1,3-dienyl)dimethylsilane, (3,5-di-tert.-butyl-2-methoxyphenyl)(2,3,4,5-tetramethylcyclopenta-1,3-dienyl)dimethylsilane, (2-methoxy-5-methyl-3-phenylphenyl)(2,3,4,5-tetramethylcyclopenta-1,3-dienyl)dimethylsilane, (2-methoxy-5-methyl-3-trimethylsilylphenyl)(2,3,4,5-tetramethylcyclopenta-1,3-dienyl)dimethylsilane, (3-tert.- butyldimethylsilyl-2-methoxy-5-methylphenyl)(2,3,4,5-tetramethylcyclopenta-1,3-dienyl)dimethylsilane, (3,5-diamyl-2-methoxyphenyl)(2,3,4,5-tetramethylcyclopenta-1,3-dienyl)dimethylsilane, (3-tert.-butyl-2,5-dimethoxyphenyl)(2,3,4,5-tetramethylcyclopenta-1,3-dienyl)dimethylsilane, (5-tert.-butyl-3-chloro-6-methoxyphenyl)(2,3,4,5-tetramethylcyclopenta-1,3-dienyl)dimethylsilane, (tert.-butylcyclopenta-1,3-dienyl)(2-methoxyphenyl)dimethylsilane, (tert.-butylcyclopenta-1,3-dienyl)(2-methoxy-3-methylphenyl)dimethylsilane, (tert.-butylcyclopenta-1,3-dienyl)(2-methoxy-3,5-dimethylphenyl)dimethylsilane, (tert.-butylcyclopenta-1,3-dienyl)(3-tert.-butyl-2-methoxyphenyl)dimethylsilane, (tert.-butylcyclopenta-1,3-dienyl)(3-tert.-butyl-2-methoxy-5-methylphenyl)dimethylsilane, (tert.-butylcyclopenta-1,3-dienyl)(3,5-di-tert.-butyl-2-methoxyphenyl)dimethylsilane, (tert.-butylcyclopenta-1,3-dienyl)(2-methoxy-5-methyl-3-phenylphenyl)dimethylsilane, (tert.-butylcyclopenta-1,3-dienyl)(2-methoxy-5-methyl-3-trimethylsilylphenyl)dimethylsilane, (tert.-butylcyclopenta-1,3-dienyl)(3-tert.-butyldimethylsilyl-2-methoxy-5-methylphenyl)dimethylsilane, (3,5-diamyl-2-methoxyphenyl)(tert.-butylcyclopenta-1,3-dienyl)dimethylsilane, (tert.-butylcyclopenta-1,3-dienyl)(3-tert.-butyl-2,5-dimethoxyphenyl)dimethylsilane, (5-tert.-butyl-3-chloro-6-methoxyphenyl)(tert.-butylcyclopenta-1,3-dienyl)dimethylsilane, (2-methoxyphenyl)(trimethylsilylcyclopenta-1,3-dienyl)dimethylsilane, (2-methoxy-3-methylphenyl)(trimethylsilylcyclopenta-1,3-dienyl)dimethylsilane, (2-methoxy-3,5-dimethylphenyl)(trimethylsilylcyclopenta-1,3-dienyl)dimethylsilane, (3-tert.-butyl-2-methoxyphenyl)(trimethylsilylcyclopenta-1,3-dienyl)dimethylsilane, (3-tert.-butyl-2-methoxy-5-methylphenyl)(trimethylsilylcyclopenta-1,3-dienyl)dimethylsilane, (3,5-di-tert.-butyl-2-methoxyphenyl)(trimethylsilylcyclopenta-1,3-dienyl)dimethylsilane, (2-methoxy-5-methyl-3-phenylphenyl)(trimethylsilylcyclopenta-1,3-dienyl)dimethylsilane, (2-methoxy-5-methyl-3-trimethylsilylphenyl)(trimethylsilylcyclopenta-1,3-dienyl)dimethylsilane, (3-tert.-butyldimethylsilyl-2-methoxy-5-methylphenyl)(trimethylsilylcyclopenta-1,3-dienyl)dimethylsilane, (3,5-diamyl-2-methoxyphenyl)(trimethylsilylcyclopenta-1,3-dienyl)dimethylsilane, (3-tert.-butyl-2,5-dimethoxyphenyl)(trimethylsilylcyclopenta-1,3-dienyl)dimethylsilane, (5-tert.-butyl-3-chloro-6-methoxyphenyl)(trimethylsilylcyclopenta-1,3 -dienyl)dimethylsilane (inden-1-yl)(2-methoxyphenyl)dimethylsilane, (inden-2-yl)(2-methoxyphenyl)dimethylsilane, (inden-1-yl)(2-methoxy-3-methylphenyl)dimethylsilane, (inden-2-yl)(2-methoxy-3-methylphenyl)dimethylsilane, (inden-1-yl)(2-methoxy-3,5-dimethylphenyl)dimethylsilane, (inden-2-yl)(2-methoxy-3,5-dimethylphenyl)dimethylsilane, (3-tert.-butyl-2-methoxyphenyl)(inden-1-yl)dimethylsilane, (3-tert.-butyl-2-methoxyphenyl)(inden-2-yl)dimethylsilane, (3-tert.-butyl-2-methoxy-5-methylphenyl)(inden-1-yl)dimethylsilane, (3-tert.-butyl-2-methoxy-5-methylphenyl)(inden-2-yl)dimethylsilane, (3,5-di-tert.-butyl-2-methoxyphenyl)(inden-1-yl)dimethylsilane, (3,5-di-tert.-butyl-2-methoxyphenyl)(inden-2-yl)dimethylsilane, (inden-1-yl)(2-methoxy-5-methyl-3-phenylphenyl)dimethylsilane, (inden-2-yl)(2-methoxy-5-methyl-3-phenylphenyl)dimethylsilane, (inden-1-yl)(2-methoxy-5-methyl-3-trimethylsilylphenyl)dimethylsilane, (inden-2-yl)(2-methoxy-5-methyl-3-trimethylsilylphenyl)dimethylsilane, (3-tert.-butyl-2-methoxy-5-methylphenyl)(inden-1-yl)dimethylsilane, (3-tert.-butyl-2-methoxy-5-methylphenyl) (inden-2-yl)dimethylsilane, (3,5-diamyl-2-methoxyphenyl)(inden-1-yl)dimethylsilane, (3,5-diamyl-2-methoxyphenyl)(inden-2-yl)dimethylsilane, (3-tert.-butyl-2,5-dimethoxyphenyl)(inden-1-yl)dimethylsilane, (3-tert.-butyl-2,5-dimethoxyphenyl)(inden-2-yl)dimethylsilane, (5-tert.-butyl-3-chloro-6-methoxyphenyl)(inden-1-yl)dimethylsilane, (5-tert.-butyl-3-chloro-6-methoxyphenyl)(inden-2 -yl)dimethylsilane, (9H-fluoren-9-yl)(2-methoxyphenyl)dimethylsilane, (9H-fluoren-9-yl)(2-methoxy-3-methylphenyl)dimethylsilane, (9H-fluoren-9-yl)(2-methoxy-3,5-dimethylphenyl)dimethylsilane, (3-tret.-butyl-2-methoxyphenyl)(9H-fluoren-9-yl)dimethylsilane, (3-tret.-butyl-2-methoxy-5-methylphenyl)(9H-fluoren-9-yl)dimethylsilane, (3,5-di-tret.-butyl-2-methoxyphenyl)(9H-fluoren-9-yl)dimethylsilane, (9H-fluoren-9-yl)(2-methoxy-5-methyl-3-phenylphenyl)dimethylsilane, (9H-fluoren-9-yl)(2-methoxy-5-methyl-3-trimethylsilylphenyl)dimethylsilane, (3-tret.-butyldimethylsilyl-2-methoxy-5-methylphenyl)(9H-fluoren-9-yl)dimethylsilane, (3,5-diamyl-2-methoxyphenyl)(9H-fluoren-9-yl)dimethylsilane, (3-tret.-butyl-2,5-dimethoxyphenyl)(9H-fluoren-9-yl)dimethylsilane, (5-tret.-butyl-3-chloro-6-methoxyphenyl)(9H-fluoren-9-yl)dimethylsilane, (2-allyloxyphenyl)(cyclopenta-1,3-dienyl)dimethylsilane, (2-allyloxy-3-methylphenyl)(cyclopenta-1,3-dienyl)dimethylsilane, (2-allyloxy-3,5-dimethylphenyl)(cyclopenta-1,3-dienyl)dimethylsilane, (2-allyloxy-3-tert.-butylphenyl)(cyclopenta-1,3-dienyl)dimethylsilane, (2-allyloxy-3-tert.-butyl-5-methylphenyl)(cyclopenta-1,3-dienyl)dimethylsilane, (2-allyloxy-3,5-di-tert.-butylphenyl)(cyclopenta-1,3-dienyl)dimethylsilane, (2-allyloxy-5-methyl-3-phenylphenyl)(cyclopenta-1,3-dienyl)dimethylsilane, (2-allyloxy-5-methyl-3-trimethylsilylphenyl)(cyclopenta-1,3-dienyl)dimethylsilane, (2-allyloxy-3-tert.-butyldimethylsilyl-5-methylphenyl)(cyclopenta-1,3-dienyl)dimethylsilane, (2-allyloxy-3,5-diamylphenyl)(cyclopenta-1,3-dienyl)dimethylsilane, (2-allyloxy-3-tert.-butyl-5-methoxyphenyl)(cyclopenta-1,3-dienyl)dimethylsilane, (6-allyloxy-5-tert.-butyl-3-chlorophenyl)(cyclopenta-1,3-dienyl)dimethylsilane, (2-allyloxyphenyl)(methylcyclopenta-1,3-dienyl)dimethylsilane, (2-allyloxy-3-methylphenyl)(methylcyclopenta-1,3-dienyl)dimethylsilane, (2-allyloxy-3,5-dimethylphenyl)(methylcyclopenta-1,3-dienyl)dimethylsilane, (2-allyloxy-3-tert.-butylphenyl)(methylcyclopenta-1,3-dienyl)dimethylsilane, (2-allyloxy-3-tert.-butyl-5-methylphenyl)(methylcyclopenta-1,3-dienyl)dimethylsilane, (2-allyloxy-3,5-di-tert.-butylphenyl)(methylcyclopenta-1,3-dienyl)dimethylsilane, (2-allyloxy-5-methyl-3-phenylphenyl)(methylcyclopenta-1,3-dienyl)dimethylsilane, (2-allyloxy-5-methyl-3-trimethylsilylphenyl)(methylcyclopenta-1,3-dienyl)dimethylsilane, (2-allyloxy-3-tert.-butyldimethylsilyl-5-methylphenyl)(methylcyclopenta-1,3-dienyl)dimethylsilane, (2-allyloxy-3,5-diamylphenyl)(methylcyclopenta-1,3-dienyl)dimethylsilane, (2-allyloxy-3-tert.-butyl-5-methoxyphenyl)(methylcyclopenta-1,3-dienyl)dimethylsilane, (6-allyloxy-5-tert.-butyl-3-chlorophenyl)(methylcyclopenta-1,3-dienyl)dimethylsilane, (2-allyloxyphenyl)(2,3,4,5-tetramethylcyclopenta-1,3-dienyl)dimethylsilane, (2-allyloxy-3-methylphenyl)(2,3,4,5-tetramethylcyclopenta-1,3-dienyl)dimethylsilane, (2 -allyloxy-3,5-dimethylphenyl)(2,3,4,5-tetramethylcyclopenta-1,3-dienyl)dimethylsilane, (2-allyloxy-3-tert.-butylphenyl)(2,3,4,5-tetramethylcyclopenta-1,3-dienyl)dimethylsilane, (2-allyloxy-3-tert.-butyl-5-methylphenyl)(2,3,4,5-tetramethylcyclopenta-1,3-dienyl)dimethylsilane, (2-allyloxy-3,5-di-tert.-butylphenyl)(2,3,4,5-tetramethylcyclopenta-1,3-dienyl)dimethylsilane, (2-allyloxy-5-methyl-3-phenylphenyl)(2,3,4,5-tetramethylcyclopenta-1,3-dienyl)dimethylsilane, (2-allyloxy-5-methyl-3-trimethylsilylphenyl)(2,3,4,5-tetramethylcyclopenta-1,3-dienyl)dimethylsilane, (2-allyloxy-3-tert.-butyldimethylsilyl-5-methylphenyl)(2,3,4,5-tetramethylcyclopenta-1,3-dienyl)dimethylsilane, (2-allyloxy-3,5-diamylphenyl)(2,3,4,5-tetramethylcyclopenta-1,3-dienyl)dimethylsilane, (2-allyloxy-3-tert.-butyl-5-methoxyphenyl)(2,3,4,5-tetramethylcyclopenta-1,3-dienyl)dimethylsilane, (6-allyloxy-5-tert.-butyl-3-chlorophenyl)(2,3,4,5-tetramethylcyclopenta-1,3-dienyl)dimethylsilane, (2-allyloxyphenyl)(tert.-butylcyclopenta-1,3-dienyl) dimethylsilane, (2-allyloxy-3-methylphenyl)(tert.-butylcyclopenta-1,3-dienyl)dimethylsilane, (2-allyloxy-3,5-dimethylphenyl)(tert.-butylcyclopenta-1,3-dienyl)dimethylsilane, (2-allyloxy-3-tert.-butylphenyl)(tert.-butylcyclopenta-1,3-dienyl)dimethylsilane, (2-allyloxy-3-tert.-butyl-5-methylphenyl)(tert.-butylcyclopenta-1,3-dienyl)dimethylsilane, (2-allyloxy-3,5-di-tert.-butylphenyl)(tert.butylcyclopenta- 1,3-dienyl)dimethylsilane, (2-allyloxy-5-methyl-3-phenylphenyl)(tert.-butylcyclopenta-1,3-dienyl)dimethylsilane, (2-allyloxy-5-methyl-3-trimethylsilylphenyl)(tert.-butylcyclopenta-1,3-dienyl)dimethylsilane, (2-allyloxy-3-tert.-butyldimethylsilyl-5-methylphenyl)(tert.-butylcyclopenta-1,3-dienyl)dimethylsilane, (2-allyloxyp-3,5-dimaylhenyl)(tert.-butylcyclopenta-1,3-dienyl)dimethylsilane, (2-allyloxy-3-tert.-butyl-5-methoxyphenyl)(tert.-butylcyclopenta-1,3-dienyl)dimethylsilane, (6-allyloxy-5-tert.-butyl-3-chlorophenyl)(tert.-butylcyclopenta-1,3-dienyl)dimethylsilane, (2-allyloxyphenyl)(trimethylsilylcyclopenta-1,3-dienyl)dimethylsilane, (2-allyloxy-3-methylphenyl)(trimethylsilylcyclopenta-1,3-dienyl)dimethylsilane, (2-allyloxy-3,5-dimethylphenyl)(trimethylsilylcyclopenta-1,3-dienyl)dimethylsilane, (2-allyloxy-3-tert.-butylphenyl)(trimethylsilylcyclopenta-1,3-dienyl)dimethylsilane, (2-allyloxy-3-tert.-butyl-5-methylphenyl)(trimethylsilylcyclopenta-1,3-dienyl)dimethylsilane, (2-allyloxy-3,5-di-tert.-butylphenyl)(trimethylsilylcyclopenta-1,3-dienyl)dimethylsilane, (2-allyloxy-5-methyl-3-phenylphenyl)(trimethylsilylcyclopenta-1,3-dienyl)dimethylsilane, (2-allyloxy-5-methyl-3-trimethylsilylphenyl)(trimethylsilylcyclopenta-1,3 -dienyl)dimethylsilane, (2-allyloxy-3-tert.-butyldimethylsiyl-5-methylphenyl)(trimethylsilylcyclopenta-1,3-dienyl)dimethylsilane, (2-allyloxy-3,5-diamylphenyl)(trimethylsilylcyclopenta-1,3-dienyl)dimethylsilane, (2-allyloxy-3-tert.-butyl-5-methoxyphenyl)(trimethylsilylcyclopenta-1,3-dienyl)dimethylsilane, (6-allyloxy-5-tert.-butyl-3-chlorophenyl)(trimethylsilylcyclopenta-1,3-dienyl)dimethylsilane, (2-allyloxyphenyl)(inden-1-yl)dimethylsilane, (2-allyloxyphenyl)(inden-2-yl)dimethylsilane, (2-allyloxy-3-methylphenyl)(inden-1-yl)dimethylsilane, (2-allyloxy-3-methylphenyl)(inden-2-yl)dimethylsilane, (2-allyloxy-3,5-dimethylphenyl)(inden-1-yl)dimethylsilane, (2-allyloxy-3,5-dimethylphenyl)(inden-2-yl)dimethylsilane, (2-allyloxy-3-tert.-butylphenyl)(inden-1-yl)dimethylsilane, (2-allyloxy-3-tert.-butylphenyl)(inden-2-yl)dimethylsilane, (2-allyloxy-3-tert.-butyl-5-methylphenyl)(inden-1-yl)dimethylsilane, (2-allyloxy-3-tert.-butyl-5-methylphenyl)(inden-2-yl)dimethylsilane, (2-allyloxy-3,5-di-tert.-butylphenyl)(inden-1-yl)dimethylsilane, (2-allyloxy-3,5-di-tert.-butylphenyl)(inden-2-yl)dimethylsilane, (2-allyloxy-5-methyl-3-phenylphenyl)(inden-1-yl)dimethylsilane, (2-allyloxy-5-methyl-3-phenylphenyl)(inden-2-yl)dimethylsilane, (2-allyloxy-5-methyl-3-trimethylsilylphenyl)(inden-1-yl) dimethylsilane, (2-allyloxy-5-methyl-3-trimethylsilylphenyl)(inden-2-yl)dimethylsilane, (2-allyloxy-3-tert.-butyldimethylsilyl-5-methylphenyl) (inden- 1-yl)dimethylsilane, (2-allyloxy-3-tert.-butyldimethylsilyl-5-methylphenyl)(inden-2-yl) dimethylsilane, (2-allyloxy-3,5-diamylphenyl)(inden-1-yl) dimethylsilane, (2-allyloxy-3,5-diamylphenyl)(inden-2-yl) dimethylsilane, (2-allyloxy-3-tert.-butyl-5-methoxyphenyl)(inden-1-yl)dimethylsilane, (2-allyloxy-3-tert.-butyl-5-methoxyphenyl)(inden-2-yl)dimethylsilane, (6-allyloxy-5-tert.-butyl-3-chlorophenyl)(inden-1-yl)dimethylsilane, (6-allyloxy-5-tert.-butyl-3-chlorophenyl)(inden-2-yl)dimethylsilane, (2-allyloxyphenyl)(9H-fluoren-9-yl)dimethylsilane, (2-allyloxy-3-methylphenyl)(9H-fluoren-9-yl)dimethylsilane, (2-allyloxy-3,5-dimethylphenyl)(9H-fluoren-9-yl)dimethylsilane, (2-allyloxy-3-tert.-butylphenyl)(9H-fluoren-9-yl)dimethylsilane, (2-allyloxy-3-tert.-butyl-5-methylphenyl)(9H-fluoren-9-yl) dimethylsilane, (2-allyloxy-3,5-di-tert.-butylphenyl)(9H-fluoren-9-yl)dimethylsilane, (2-allyloxy-5-methyl-3-phenylphenyl)(9H-fluoren-9-yl)dimethylsilane, (2-allyloxy-5-methyl-3-trimethylsilylphenyl)(9H-fluoren-9-yl) dimethylsilane, (2-allyloxy-3-tert.-butyldimethylsilyl-5-methylphenyl)(9H-fluoren-9-yl)dimethylsilane, (2-allyloxy-3,5-diamylphenyl)(9H-fluoren-9-yl)dimethylsilane, (2-allyloxy-3-tert.-butyl-5-methoxyphenyl)(9H-fluoren-9-yl)dimethylsilane, (6-allyloxy-5-tert.-butyl-3-chlorophenyl)(9H-fluoren-9-yl)dimethylsilane, (1-allyloxynaphthalen-2-yl)dimethyl(1,2,3,4-tetramethylcyclopentadienyl)silane, etc. analogous compounds to the above compounds in which a ethoxy or an allyloxy group is replaced by a benzyloxy group, an ethoxy group, a trimethylsilyloxy grou, a tert.-butyldimethylsilyloxy group or a methoxymethoxy group; or a dimethylsilane group is replaced by a diethylsilane group, a diphenylsilane group or a dimethoxysilane group; or a cyclopentadienyl group is replaced by a dimethylcyclopentadienyl group, a trimethylcyclopentadienyl group, a n-propylcyclopentadienyl group, an isopropylcyclopentadienyl group, a n-butylcyclopentadienyl group, an isobutylcyclopentadienyl group, a sec.-butylcyclopentadienyl group, a tert.-butyldimethylsilylcyclopentadienyl group, a phenylcyclopentadienyl group or a methylindenyl group; or a 2-methoxyphenyl group is replaced by a 3-phenyl-2-methoxyphenyl group, a 3-trimethylsilyl-2-methoxyphenyl group or a 3-tert.-butyldimethylsilyl-2-methoxyphenyl group.

Such compounds (3) may contain a plurality of isomers which are due to the positions of substituents and/or the positions of double bonds in a cyclopentadiene moiety of the substituent Cp. The compound (3) of the present invention includes all such isomers.

INDUSTRIAL APPLICABILITY

According to the proceeses of the present invention, a wide variety of cyclopentadienyl metal salts and also the derivatives of cyclopentadiene can be prepared at a high conversion and a high selectivity without the use of expensive reagents and low-temperature facilities.

EXAMPLES

The present invention will be illustrated by the following examples, which do not limit the scope of the invention in any way.

Example 1

Tetramethylcyclopentadiene (1.16 g; purity: 86%; pure compound: 1.00 g) was dissolved in tetrahydrofuran (20 ml). Then, sodium hydride (washed with hexane) (0.197 g) and diisopropylamine (0.0828 g) were added to the solution, followed by refluxing for 7 hours.

After cooling the reaction mixture to room temperature, dichlorodimethylsilane (3.16 g) was added to the reaction mixture, and stirred for 30 minutes to convert tetramethylcyclopentadienylsodium to chlorodimethyl(tetramethylcyclopentadienyl)silane. Chlorodimethyl(tetramethylcyclopentadienyl)silane was quantitatively analyzed by gas chromatography, and the yield of tetramethylcyclopentadienylsodium was calculated. The yield was 53%.

Example 2

The same procedures as those in Example 1 were repeated except that 2,2,6,6-tetramethylpiperidine (0.0578 g) was used in place of diisopropylamine, and the refluxing time was changed from 7 hours to 5 hours. The yield of tetramethylcyclopentadienylsodium was 33%.

Example 3

The same procedures as those in Example 1 were repeated except that butylamine (0.0299 g) was used in place of diisopropylamine, and the refluxing time was changed from 7 hours to 5 hours. The yield of tetramethylcyclopentadienylsodium was 18%.

Comparative Example 1

The same procedures as those in Example 1 were repeated except that no diisopropylamine was used. The yield of tetramethylcyclopentadienylsodium was 0%.

Comparative Example 2

The same procedures as those in Example 1 were repeated except that potassium tert.-butoxide (1.84 g) was used in place of the combination of sodium hydride and diisopropylamine. The yield of tetramethylcyclopentadienylsodium was 0%.

Example 4

Sodium hydride (containing mineral oil; the content of sodium hydride: 60%) (0.41 g) and aniline (0.033 g) were added to the solution of tetramethylcyclopentadiene (0.63 g) in tetrahydrofuran (15 ml), and stirred at 40° C. for 4 hours. Thus, tetramethylcyclopentadienylsodium was obtained in the form of a solution in tetrahydrofuran.

Methyl iodide (2.8 g) was added to the obtained reaction solution, and stirred for 30 minutes to convert tetramethylcyclopentadienylsodium to pentamethylcyclopentadiene. The content of pentamethylcyclopentadiene was 0.62 g, when measured by gas chromatography. Thus, the yield of tetramethylcyclopentadienylsodium was 88%.

Example 5

The same procedures as those in Example 4 were repeated except that potassium hydride (containing mineral oil; the content of potassium hydride: 35%) (1.17 g) was used in place of sodium hydride. The yield of tetramethylcyclopentadienylpotassium was 90%

Example 6

Sodium hydride (containing mineral oil; the content of sodium hydride: 60%) (0.80 g) and m-chloroaniline (0.064 g) were added to the solution of tetramethylcyclopentadiene (1.34 g; purity: 91.3%; pure compound: 1.22 g) dissolved in tetrahydrofuran (6.73 g), and stirred at 50° C. for one hour. Thus, tetramethylcyclopentadienylsodium was obtained in the form of a solution in tetrahydrofuran.

Methyl iodide (2.8 g) was added to the obtained reaction solution, and stirred for 30 minutes to convert tetramethylcyclopentadienylsodium to pentamethylcyclopentadiene. When the content of pentamethylcyclopentadiene was measured by gas chromatography, the yield of tetramethylcyclopentadienylsodium was 83%.

Example 7

The same procedures as those in Example 6 were repeated except that cyclopentadiene (0.661 g) was used in place of tetramethylcyclopentadiene, and butylamine (0.037 g) was used in place of m-chloroaniline. The yield of cyclopentadienylsodium was 99%.

Example 8

Sodium hydride (containing mineral oil; the content of sodium hydride: 60%) (0.80 g) and aniline (0.046 g) were added to the solution of trimethylcyclopentadiene (1.08 g) dissolved in tetrahydrofuran (6.12 g), and stirred at 50° C. for 3 hours. Thus, trimethylcyclopentadienylsodium was obtained in the form of a solution in tetrahydrofuran.

Methyl iodide (2.8 g) was added to the obtained reaction solution, and stirred for 30 minutes to convert trimethylcyclopentadienylsodium to tetramethylcyclopentadiene. When the content of tetramethylcyclopentadiene was measured by gas chromatography, the yield of trimethylcyclopentadienylsodium was 90%.

Example 9

The same procedures as those in Example 8 were repeated except that 2-cyclopentadienyl-2-fluorenylpropane (2.72 g) was used in place of trimethylcyclopentadiene, the amount of tetrahydrofuran was changed from 6.12 g to 15.4 g, the amount of sodium hydride (containing mineral oil; the content of sodium hydride: 60%) was changed from 0.80 g to 1.60 g, the amount of aniline was changed from 0.046 g to 0.092 g, and the amount of methyl iodide was changed from 2.8 g to 5.6 g. The yield of 2-cyclopentadienyl-2-fluorenylpropane disodium salt was 93%.

Example 10

The same procedures as those in Example 8 were repeated except that bistrimethylcyclopentadienyldimethylsilane (2.73 g) was used in place of trimethylcyclopentadiene, the amount of tetrahydrofuran was changed from 6.12 g to 15.5 g, the amount of sodium hydride (containing mineral oil; the content of sodium hydride: 60%) was changed from 0.80 g to 1.60 g, the amount of aniline was changed from 0.046 g to 0.092 g, and the amount of methyl iodide was changed from 2.8 g to 5.6 g. The yield of bistrimethylcyclopentadienyldimethylsilane disodium salt was 88%.

Example 11

The same procedures as those in Example 8 were repeated except that 1,2-bisindenylethane (2.58 g) was used in place of trimethylcyclopentadiene, the amount of tetrahydrofuran was changed from 6.12 g to 14.6 g, the amount of sodium hydride (containing mineral oil; the content of sodium hydride: 60%) was changed from 0.80 g to 1.60 g, the amount of aniline was changed from 0.046 g to 0.092 g, and the amount of methyl iodide was changed from 2.8 g to 5.6 g. The yield of 1,2-bisindenylethane disodium salt was 92%.

Example 12

Sodium hydride (containing mineral oil; the content of sodium hydride: 60%) (3.30 g) and aniline (0.237 g) were added to the solution of tetramethylcyclopentadiene (5.01 g) dissolved in tetrahydrofuran (45 ml), and stirred at 40° C. for 4 hours. Thus, tetramethylcyclopentadienylsodium was obtained in the form of a solution in tetrahydrofuran.

Methyl iodide (8.0 g) was added to the obtained reaction solution, and stirred for 30 minutes to convert tetramethylcyclopentadienylsodium to pentamethylcyclopentadiene. The content of pentamethylcyclopentadiene was 4.80 g when measured by gas chromatography. Thus, the yield of tetramethylcyclopentadienylsodium was 86%.

Example 13

Sodium hydride (containing mineral oil; the content of sodium hydride: 60%) (2.50 g) and aniline (0.237 g) were added to the solution of tetramethylcyclopentadiene (5.01 g) dissolved in tetrahydrofuran (28 ml), and stirred at 40° C. for 4 hours. Thus, tetramethylcyclopentadienylsodium was obtained in the form of a solution in tetrahydrofuran.

Methyl iodide (8.0 g) was added to the obtained reaction solution, and stirred for 30 minutes to convert tetramethylcyclopentadienylsodium to pentamethylcyclopentadiene. The content of pentamethylcyclopentadiene was 4.78 g when measured by gas chromatography. Thus, the yield of tetramethylcyclopentadienylsodium was 85%.

Example 14

Sodium hydride (containing mineral oil; the content of sodium hydride: 60 wt. %) (0.60 g) was suspended in tetrahydrofuran (6.91 g), and then aniline (0.047 g) was dropwise added to the suspension at 25° C. After heating to 50° C., the suspension was stirred for 10 minutes. Thereafter, tetramethylcyclopentadiene (1.22 g) was dropwise added to the suspension while maintaining the suspension at 50° C., followed by stirring for one hour. Thus, tetramethylcyclopentadienylsodium was obtained. After cooling the above solution to 20° C., the solution of (2-allyloxy-3-tert.-butyl-5-methylphenyl)chlorodimethylsilane (3.86 g; purity: 73%; pure compound: 2.82 g) in toluene was dropwise added to the above solution, followed by stirring for 2 hours.

After adding water (3 g) to the reaction mixture, the solvent was evaporated off. Toluene (10 g) and water (3 g) were added to the residual oil, and the mixture was separated. The organic layer was concentrated, and (2-allyloxy-3-tert.-butyl-5-methylphenyl)dimethyl(2,3,4,5-tetramethylcyclopentadienyl)silane (4.97 g; purity: 63%; pure compound: 3.13 g) was obtained. The yield was 82% based on tetramethylcyclopentadiene.

Example 15

Potassium hydride (containing mineral oil; the content of sodium hydride: 35%) (3.00 g) was suspended in tetrahydrofuran (18 ml), and then 4-methylaniline (0.056 g) was dropwise added to the suspension at 10° C., followed by stirring for 10 minutes. Thereafter, the solution of tetramethylcyclopentadiene (1.22 g) dissolved in tetrahydrofuran (6 ml) was dropwise added to the suspension, and heated to 25° C., followed by stirring for one hour. Thus, tetramethylcyclopentadienylpotassium was obtained. To this solution, the solution of (2-allyloxy-3-tert.-butyl-5-methylphenyl)chlorodimethylsilane (3.99 g; purity: 70.7%; pure compound: 2.82 g) dissolved in tetrahydrofuran (3 ml) was dropwise added, followed by stirring for one hour.

After adding water (15 ml) and hexane (15 ml) to the reaction mixture, the mixture was separated. The organic layer was concentrated, and (2-allyloxy-3-tert.-butyl-5-methylphenyl)dimethyl(2,3,4,5-tetramethylcyclopentadienyl)silane (pure compound: 3.23 g) was obtained. The yield was 85% based on tetramethylcyclopentadiene.

What is claimed is:

1. A process for the preparation of a cyclopentadienyl metal salt comprising the step of reacting a cyclopentadiene and a metal hydride in the presence of an amine compound.

2. A process according to claim 1, wherein said amine compound is a primary amine or a secondary amine.

3. A process according to claim 2, wherein said primary amine is a primary aniline.

4. A process according to any one of claims 1 to 3, wherein an amount of said amine compound is from 0.001 to 2 moles per one mole of said metal hydride.

5. A process according to any one of claims 1 to 3, wherein an amount of said amine compound is from 0.01 to 0.5 mole per one mole of said metal hydride.

6. A process according to any one of claims 1 to 3, wherein an amount of said metal hydride is from 0.5 to 3 moles per one mole of said cyclopentadiene.

7. A process according to any one of claims 1 to 3, wherein said metal hydride contains mineral oils.

8. A process according to any one of claims 1 to 3, wherein a reaction temperature is from 10 to 60° C.

9. A process according to any one of claims 1 to 3, wherein said cyclopentadiene is a compound of the formula (2a):

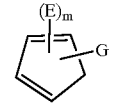

wherein m is an integer of 0 to 5, E groups are the same or different and independently represent a $C_1$–$C_8$ alkyl group, a phenyl group, a naphthyl group, or a tri-substituted silyl group having substituents selected from the group consisting of a $C_1$–$C_4$ alkyl group and a phenyl group, provided that, when two E groups are present on adjacent carbon atoms, they may be bonded at their ends to form a benzene ring, a cyclohexane ring or a cyclohexene ring, which is condensed with the cyclopentadienyl ring, G is a hydrogen atom when m is 5, or when m is 0 to 4, G is a hydrogen atom or a group of the formula (2b):

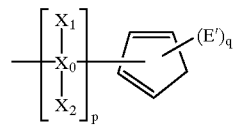

wherein p is 1 or 2, q is an integer of 0 to 4, $X_0$ is a carbon atom or a silicon atom, $X_1$ and $X_2$ are the same or different and independently represent a hydrogen atom, a $C_1$–$C_4$ alkyl group or a phenyl group, E' is a substituent selected from those defined for E, provided that when $X_0$ is a silicon atom, $X_1$ and $X_2$ are not hydrogen atoms.

10. A process according to claim 9, wherein m is an integer of 2 to 5, or m is 1 and G is a group of the formula (2b).

11. A process for the preparation of a cyclopentadiene derivative of the formula (3):

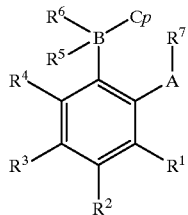
(3)

wherein

A is an atom of the 16 group of the Periodic Table,

B is an atom of the 14 group of the Periodic Table, $R^1$, $R^2$, $R^3$, $R^4$, $R^5$ and $R^6$ are the same or different and independently represent a hydrogen atom, a fluorine atom, a $C_1$–$C_{20}$ alkyl group which may optionally be substituted with a fluorine atom, a $C_7$–$C_{20}$ aralkyl group which may optionally be substituted with a fluorine atom, a $C_6$–$C_{20}$ aryl group which may optionally be substituted with a fluorine atom, a $C_1$–$C_{20}$ substituted silyl group, a $C_1$–$C_{20}$ alkoxyl group which may optionally be substituted with a fluorine atom, a $C_7$–$C_{20}$ aralkyloxyl group which may optionally be substituted with a fluorine atom, a $C_6$–$C_{20}$ aryloxyl group which may optionally be substituted with a fluorine atom, or a $C_2$–$C_{20}$ di-substituted amino group which may optionally be substituted with a fluorine atom, provided that any two or more of $R^1$, $R^2$, $R^3$, $R^4$, $R^5$ and $R^6$ may together form a ring, $R^7$ is a hydrocarbon group which may optionally be substituted with a fluorine atom, or a tri-substituted silyl group, and Cp is a cyclopetadiene ring comprising the step of reacting a halide compound of the formula (1):

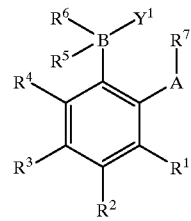
(1)

wherein A, B, $R^1$, $R^2$, $R^3$, $R^4$, $R^5$, $R^6$ and $R^7$ are the same as defined above, and $Y^1$ is a chlorine atom, a bromine atom or an iodine atom
with a cyclopentadiene of the formula (2):

$$HCp \qquad (2)$$

wherein Cp is the same as defined above, in the presence of a metal hydride and an amine compound.

12. A process according to claim 11, wherein said cyclopentadiene of the formula (2) is reacted with said metal hydride in the presence of said amine compound, and then reacted with said halide compound of the formula (1).

13. A process according to claim 11 or 12, wherein said cyclopentadiene of the formula (2) is a compound of the formula (2a) in claim 9.

14. A process according to claim 11 or 12, wherein said amine compound is a primary amine or a secondary amine.

15. A process according to claim 14, wherein said primary amine is a primary aniline.

16. A process according to claim 12, wherein an amount of said amine compound is from 0.001 to 2 moles per one mole of said metal hydride.

17. A process according to claim 12, wherein an amount of said amine compound is from 0.01 to 0.5 mole per one mole of said metal hydride.

18. A process according to any one of claims 11 or 12, wherein an amount of said metal hydride is from 0.5 to 3 moles per one mole of said compound of the formula (2).

19. A process according to any one of claims 11 or 12, wherein a reaction temperature is from 10 to 60° C.

20. A process according to any one of claims 11 or 12, wherein said metal hydride contains mineral oils.

* * * * *

(12) EX PARTE REEXAMINATION CERTIFICATE (5991st)
United States Patent
Oda et al.

(10) Number: US 6,197,990 C1
(45) Certificate Issued: Nov. 6, 2007

(54) PROCESS FOR PRODUCING CYCLOPENTADIENYL METAL SALT AND PROCESS FOR PRODUCING CYCLOPENTADIENE DERIVATIVES BY UTILIZING THE SAME

(75) Inventors: Yoshiaki Oda, Toyonaka (JP); Kazuhiro Yamauchi, Ibaraki (JP); Hidenori Hanaoka, Osaka (JP); Hiroshi Souda, Ibaraki (JP)

(73) Assignee: Sumitomo Chemical Company, Limited, Chuo-Ku, Osaka-Shi, Osaka (JP)

Reexamination Request:
No. 90/007,988, Mar. 31, 2006

Reexamination Certificate for:
Patent No.: 6,197,990
Issued: Mar. 6, 2001
Appl. No.: 09/341,498
Filed: Jul. 13, 1999

(22) PCT Filed: Jan. 14, 1998
(86) PCT No.: PCT/JP98/00110
§ 371 (c)(1),
(2), (4) Date: Jul. 13, 1999
(87) PCT Pub. No.: WO98/30567
PCT Pub. Date: Jul. 16, 1998

(30) Foreign Application Priority Data

Jan. 14, 1997 (JP) .......................... 9-005036
Jan. 14, 1997 (JP) .......................... 9-005037

(51) Int. Cl.
*C07F 1/04* (2006.01)
*C07F 1/00* (2006.01)
*C07F 7/00* (2006.01)
*C07F 7/08* (2006.01)

(52) U.S. Cl. .......................... 556/478; 556/87; 585/350
(58) Field of Classification Search .................. None
See application file for complete search history.

(56) References Cited

U.S. PATENT DOCUMENTS 4,492,655 A   1/1985   Gradeff et al.

FOREIGN PATENT DOCUMENTS

| EP | 0842939 A1 | 5/1998 |
| JP | 1-213289 A | 8/1989 |
| JP | 6-279477 A | 10/1994 |
| JP | 08-027160 A | 1/1996 |
| JP | 9-169791 A | 6/1997 |
| WO | WO 97/03992 A1 | 2/1997 |

OTHER PUBLICATIONS

International Search Report for PCT/JP/98/00110 dated May 12, 1998.
Lectures on Experimental Chemistry, vol. 18 "Organometallic Complexes", edited by the Chemical Society of Japan; Published by Maruzen Co., Ltd. 1991, p. 24–26.
"Polycyclopentadienyls," Journal of Organometallic Chemistry, 1992, 435, p. 21–28.
Chemistry Abstracts, vol. 112, No. 5, "Synthesis and proton NMR spectra of substituted cyclopendienes" Gaodeng Xuexiao Huaxue Xuebao, 1989, 10(5), 546–8 (Ch).
International Preliminary Examination Report dated Oct. 21, 1998.
Supplementary European Search Report dated Jan. 8, 2002.
Office Action issued in corresponding Japanese Patent Application dated Jul. 5, 2005.

*Primary Examiner*—Evelyn Huang

(57) ABSTRACT

A cyclopentadienyl metal salt is prepared by reacting a cyclopentadiene and a metal hydride in the presence of an amine compound. Furthermore, a derivative of a cyclopentadiene in which a phenyl group is bonded to its cyclopentadienyl moiety through an element of the 14 group of the Periodic Table is prepared using such a reaction.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 7, 14 and 20 are cancelled.

Claims 1, 3–6, 8–9, 11–13 and 15–17 are determined to be patentable as amended.

Claims 10, 18 and 19, dependent on an amended claim, are determined to be patentable.

1. A process for the preparation of a cyclopentadienyl metal salt comprising the step of reacting a cyclopentadiene and a metal hydride in the presence of [an amine compound] *a primary aniline or a secondary aniline*.

3. A process according to claim [2] *1*, wherein said [primary amine is a] primary aniline *is used*.

4. A process according to any one of claims 1 [to] *or* 3, wherein an amount of said [amine compound] *primary aniline* is from 0.001 to 2 moles per one mole of said metal hydride.

5. A process according to any one of claims 1 [to] *or* 3, wherein an amount, of said [amine compound] *aniline* is from 0.01 to 0.5 mole per one mole of said metal hydride.

6. A process according to any one of claims 1 [to] *or* 3, wherein an amount of said metal hydride is from 0.5 to 3 moles per one mole of said cyclopentadiene.

8. A process according to any one of claims 1 [to] *or* 3, wherein a reaction temperature is from 10 to 60° C.

9. A process according to any one of claims 1 [to] *or* 3, wherein said cyclopentadiene is a compound of the formula (2a):

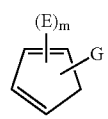

wherein m is an integer of 0 to 5, E groups are the same or different and independently represent, a $C_1$–$C_8$ alkyl group, a phenyl group, a naphthyl group, or a tri-substituted silyl group having substituents selected from the group consisting of a $C_1$–$C_4$ alkyl group and a phenyl group, provided that, when two E groups are present on adjacent carbon atoms, they may be bonded at their ends to form a benzene ring, a cyclohexane ring or a cyclohexene ring, which is condensed with the cyclopentadienyl ring, G is a hydrogen atom when m is 5, or when m is 0 to 4, G is a hydrogen atom or a group of the formula (2b):

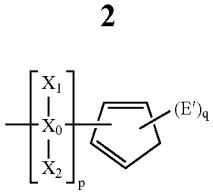

wherein p is 1 or 2, q is an integer of 0 to 4, $X_0$ is a carbon atom or a silicon atom, $X_1$ and $X_2$ are the same or different and independently represent a hydrogen atom, a $C_1$–$C_4$ alkyl group or a phenyl group, E' is a substituent selected from those defined for E, provided that when $X_0$ is a silicon atom, $X_1$ and $X_2$ are not hydrogen atoms.

11. A process for the preparation of a cyclopentadiene derivative of the formula (3):

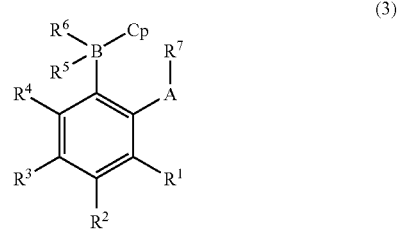

wherein
A is an atom of the 16 group of the Periodic Table,
B is an atom of the 14 group of the Periodic Table,
$R^1$, $R^2$, $R^3$, $R^4$, $R^5$ and $R^6$ are the same or different and independently represent a hydrogen atom, a fluorine atom, a $C_1$–$C_{20}$ alkyl group which may optionally be substituted with a fluorine atom, a $C_7$–$C_{20}$ aralkyl group which may optionally be substituted with a fluorine atom, a $C_6$–$C_{20}$ aryl group which may optionally be substituted with a fluorine atom, a $C_1$–$C_{20}$ substituted silyl group, a $C_1$–$C_{20}$ alkoxyl group which may optionally be substituted with a fluorine atom, a $C_7$–$C_{20}$ aralkyloxyl group which may optionally be substituted with a fluorine atom, a $C_6$–$C_{20}$ aryloxyl group which may optionally be substituted with a fluorine atom, or a $C_2$–$C_{20}$ di-substituted amino group which may optionally be substituted with a fluorine atom, provided that any two or more of $R^1$, $R^2$, $R^3$, $R^4$, $R^5$ and $R^6$ may together form a ring,
$R^7$ is a hydrocarbon group which may optionally be substituted with a fluorine atom, or a tri-substituted silyl group, and
Cp is a cyclopentadiene ring comprising the step of reacting a halide compound of the formula (1):

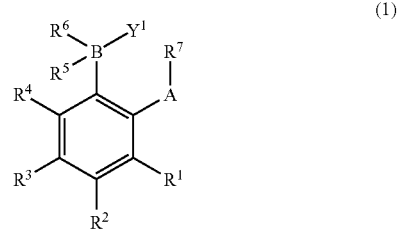

wherein A, B, $R^1$, $R^2$, $R^3$, $R^4$, $R^5$, $R^6$ and $R^7$ are the same as defined above, and $Y^1$ is a chlorine atom, a bromine atom or an iodine atom with a cyclopentadiene of the formula (2):

 (2):

wherein Cp is the same as defined above, in the presence of a metal hydride and [an amine compound] *a primary aniline or a secondary aniline*.

12. A process according to claim 11, wherein said cyclopentadiene of the formula (2) is reacted with said metal hydride in the presence of said [amine compound] *primary aniline or secondary aniline*, and then reacted with said halide compound of the formula (1).

13. A process according to claim 11 or 12, wherein said cyclopentadiene of the formula (2) is a compound of [the] formula (2a) [in claim 9]

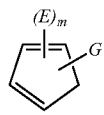

*wherein m is an integer of 0 to 5, E groups are the same or different and independently represent, a $C_1$–$C_8$ alkyl group, a phenyl group, a naphthyl group, or a tri-substituted silyl group having substituents selected from the group consisting of a $C_1$–$C_4$ alkyl group and a phenyl group, provided that, when two E groups are present on adjacent carbon atoms, they may be bonded at their ends to form a benzene ring, a cyclohexane ring or a cyclohexene ring, which is condensed with the cyclopentadienyl ring, G is a hydrogen atom when m is 5, or when m is 0 to 4, G is a hydrogen atom.*

15. A process according to claim [14] *11*, wherein said [primary amine is a] primary aniline *is used*.

16. A process according to claim 12, wherein an amount of said [amine compound] *aniline* is from 0.001 to 2 moles per one mole of said metal hydride.

17. A process according to claim 12, wherein an amount of said [amine compound] *aniline* is from 0.01 to 0.5 mole per one mole of said metal hydride.

* * * * *